United States Patent [19]

Imura et al.

[11] Patent Number: 5,708,063
[45] Date of Patent: Jan. 13, 1998

[54] PHOTOCHROMIC COMPOUND

[75] Inventors: Satoshi Imura; Tsuneyoshi Tanizawa; Takashi Kobayakawa, all of Shinnanyo, Japan

[73] Assignee: Tokuyama Corporation, Yamguchi-ken, Japan

[21] Appl. No.: 601,832

[22] Filed: Feb. 15, 1996

Related U.S. Application Data

[63] Continuation of Ser. No. 258,064, Jun. 10, 1994, abandoned.

[30] Foreign Application Priority Data

May 11, 1993 [JP] Japan ............... 5-141023

[51] Int. Cl.$^6$ .............. C08K 5/15; C08K 5/3417
[52] U.S. Cl. .............. 524/84; 524/89; 524/110
[58] Field of Search .............. 548/417; 524/84, 524/89, 110

[56] References Cited

U.S. PATENT DOCUMENTS 4,882,438  11/1989  Tanaka et al. ............ 548/407

FOREIGN PATENT DOCUMENTS 0316179  11/1988  European Pat. Off. .
2146327  4/1985  United Kingdom .

*Primary Examiner*—Kriellion S. Morgan
*Attorney, Agent, or Firm*—Birch, Stewart, Kolasch & Birch, LLP

[57] ABSTRACT

A fulgide or fulgimide compound having a cyclopropyl group as a substituent. The compound has excellent durability which changes reversibly in color from a colorless form to a colored form by the action of light containing ultraviolet rays such as sunlight or the light from a mercury lamp. There are also provided processes for its production, a composition comprising it, and its use.

14 Claims, 1 Drawing Sheet

$\delta$ (ppm)

PHOTOCHROMIC COMPOUND

This application is a continuation of application Ser. No. 08/258,064 filed on Jun. 10, 1994, now abandoned.

This invention relates to a novel compound having a photochromic action, processes for producing it, a composition comprising it, and to its use. More specifically, it relates to a novel compound having excellent durability which changes reversibly in color from a colorless form to a colored form by the action of light containing ultraviolet rays such as sunlight or the light from a mercury lamp, processes for its production, a composition comprising it, and to its use.

Photochromism, which has aroused a particular interest for the last several years, denotes a phenomenon in which when light containing ultraviolet rays such as sunlight or the light from a mercury lamp is irradiated onto a certain compound, its color rapidly changes, and when the light irradiation is stopped and the compound is placed in a dark place, its color reversibly returns to the original color. Compounds having this property are called photochromic compounds. Photochromic compounds of various structures have been synthesized and proposed, but no particular common structure has been observed in these compounds.

Under the circumstances, Japanese Laid-open Patent Application No. 155,179/1985 and the corresponding British Laid-open Patent Application No. 2,146,327 disclose a photochromic compound represented by the following formula

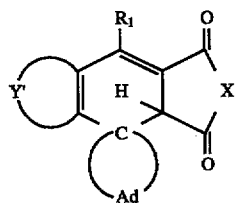

wherein

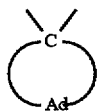

represents an adamantylidene group which may be substitued, $R_1$ represents hydrogen, an alkyl group, an aryl group, an aralkyl group or a heterocyclic group, X represents oxygen or >$NR'_1$ in which $R'_1$ represents hydrogen, an aryl group, an alkyl group or an aralkyl group, and

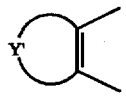

represents an aromatic group, an unsaturated heterocyclic group or a heterocyclic group to which a benzene ring is bound,
and use of the photochromic compound in a photoreactive lens.

Japanese Laid-open Patent Application No. 28,154/1990 and the corresponding U.S. Pat. No. 4,882,438 describe a fulgide compound or a fulgimide compound represented by the following formula

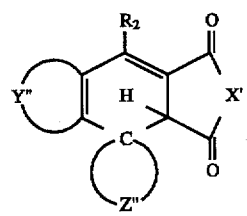

These compounds are stably colorless in a normal state. However, as soon as they undergo irradiation with sunlight or ultraviolet light, they are colored. When the irradiation stops, they return to the colorless state. Tese compounds can repeatedly exhibit the color change with good durability and hence, are compounds having excellent photochromic property. In the above fulgide compounds or fulgimide compounds,

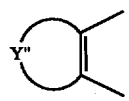

represents an aromatic hydrocarbon group or an unsaturated heterocyclic group, $R_2$ represents a hydrocarbon group or a heterocyclic group, and X' represents an imino group in which a hydrogen atom may be substituted by a specific group, or an oxygen group. Further,

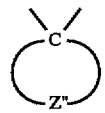

represents a norbornylidene group or an adamantylidene group which may have a substituent.

The above fulgide compounds or fulgimide compounds are, as noted above, photochromic compounds which are excellent in durability when a colored form and a colorless form are reversibly repeated. However, development of photochromic compounds having further improved durability has been demanded.

It is an object of this invention to provide a novel photochromic compound.

Another object of this invention is to provide a compound which reversibly changes from a colorless form to a colored form by the action of ultraviolet rays.

Still another object of this invention is to provide a photochromic compound having durability which can be used for along period of time.

Yet another object of this invention is to provide a photochromic compound having practical utility.

A further object of this invention is to provide industrially advantageous processes for producing the photochromic compound.

A still further object of this invention is to provide a polymeric composition comprising the photochromic compound.

Other objects of the invention will become apparent from the following description.

These objects and advantages of the invention are achieved by a novel compound represented by the following general formula [I]

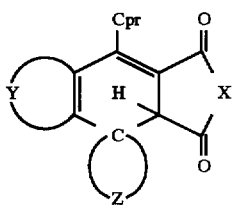 [I]

wherein

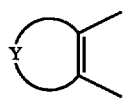

represents a divalent aromatic hydrocarbon group or a divalent unsaturated heterocyclic group each of which may have a substituent, Cpr represents a cyclopropyl group which may have a substituent,

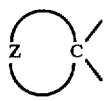

represents a norbornylidene group, a bicyclo[3.3.1] nonylidene group, or an adamantylidene group each of which may have a substituent, and X represents an oxygen atom, the group >N—$R_{11}$, the group >N—$A_1$—$B_1$—$(A_2)_m$—$(B_2)_n$—$R_{12}$, the group >N—$A_3$—$A_4$, or the group >N—$A_3$—$R_{13}$, in which $R_{11}$ represents a hydrogen atom, an alkyl group having 1 to 20 carbon atoms, or an aryl group having 6 to 10 carbon atoms, $A_1$ and $A_2$ are identical or different and each represents an alkylene group having 1 to 10 carbon atoms, an alkylidene group having 2 to 10 carbon atoms, a cycloalkylene group having 3 to 10 carbon atoms or an alkylcycloalkanediyl group having 6 to 10 carbon atoms, $B_1$ and $B_2$ are identical or different, and each represents

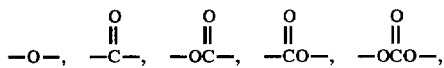

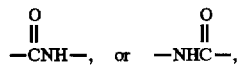

m and n, independently from each other, represent 0 or 1, provided that when m is 0, n is also 0, $R_{12}$ represents an alkyl group having 1 to 10 carbon atoms, a naphthyl group or a naphthylalkyl group having 1 to 4 carbon atoms in the alkyl moiety, the alkyl group having 1 to 10 carbon atoms being optionally substituted by 1 to 3 atoms or groups selected from the class consisting of halogen atoms, cyano groups and nitro groups, and the naphthyl or naphthylalkyl group being optionally substituted by 1 to 3 atoms or groups selected from the class consisting of halogen atoms, cyano groups, nitro groups, alkylamino groups having 1 to 3 carbon atoms, alkyl groups having 1 to 3 carbon atoms and alkoxy groups having 1 to 3 carbon atoms, $A_3$ represents an alkylene group having 1 to 10 carbon atoms, an alkylidene group having 2 to 10 carbon atoms, a cycloalkylene group having 3 to 10 carbon atoms, or an alkylcycloalkanediyl group having 6 to 10 carbon atoms, $A_4$ represents a naphthyl group which may be substituted by 1 to 3 atoms or groups selected from the class consisting of halogen atoms, cyano groups, nitro groups, alkylamino groups having 1 to 3 carbon atoms, alkyl groups having 1 to 3 carbon atoms and alkoxy groups having 1 to 3 carbon atoms, and $R_{13}$ represents a halogen atom, a cyano group or a nitro group.

The compound of the invention represented by general formula [I] will be described below in greater detail.

In general formula [I], the group

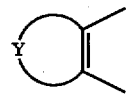

represents an aromatic hydrocarbon group or an unsaturated heterocyclic group, which may have at most 5, preferably up to 3, substituents. The aromatic hydrocarbon group has 6 to 20 carbon atoms, preferably 6 to 14 carbon atoms. Examples of the ring forming the aromatic hydrocarbon group are benzene, naphthalene and phenanthrene rings.

The unsaturated heterocyclic group may be a 5- or 6-membered hetero-monocyclic group containing 1 to 3, preferably 1 or 2, hereto atoms selected from nitrogen, oxygen and sulfur atoms, or a condensed heterocyclic group in which a benzene ring or a cyclohexene ring Is fused. Examples of the ring forming these heterocyclic groups are nitrogen-containing heterocyclic rings such as pyrrole ring, a pryidine ring, a quinoline ring, an isoquinoline ring, an imidazole ring and a benzimidazole ring; oxygen-containing heterocyclic rings such as furan ring, a benzofuran ring and a pyrane ring; sulfur-containing heterocycling rings such as a thiophene ring and a benzothiophene ring and rings containing two kinds of hetero atoms such as an oxazole ring and a thiazole ring.

As stated above, the aromatic hydrocarbon group or unsaturated heterocyclic group represented by

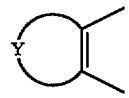

contains at most 5, preferably up to 3, substituents. Examples of the substituents include halogen atoms such as fluorine, chlorine, bromine and iodine; a hydroxyl group; a cyano group; an amino group; a nitro group; a carboxyl group; alkylamino groups having 1 to 4 carbon atoms such as methylamino and diethylamino groups; alkyl groups having 1 to 4 carbon atoms such as methyl, ethyl, propyl and t-butyl groups; halogenated lower alkyl groups containing 1 to 3 halogen atoms such as trifluoromethyl and 2-chloroethyl groups; lower alkoxy groups having 1 to 4 carbon atoms such as methoxy, ethoxy and t-butoxy groups; aryl groups having 6 to 10 carbon atoms such as phenyl, naphthyl and tolyl groups; aryloxy groups containing 6 to 14 carbon atoms such as phenoxy and 1-naphthoxy groups; aralkyl groups having 7 to 15 carbon atoms such as benzyl, phenylethyl and phenylpropyl groups; aralkoxy groups having 7 to 15 carbon atoms such as benzyloxy and phenylpropoxy groups; and alkylthio groups having 1 to 4 carbon atoms. These substituents may be of the same or different kind, and the position of substitution is not particularly limited.

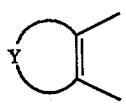

is preferably a divalent aromatic hydrocarbon group or a divalent unsaturated heterocyclic groups, each of which may be substituted by at least one atom or group selected from the class consisting of halogen atoms, a nitro group, a cyano group, an amino group, alkylthio groups having 1 to 4 carbon atoms, aryl groups having 6 to 10 carbon atoms, alkyl groups having 1 to 4 carbon atoms and alkoxy groups having 1 to 4 carbon atoms.

More preferably, it is an aryl group having 6 to 14 carbon atoms, a 5- or 6-membered hetero-monocyclic group containing 1 to 3 carbon atoms selected from nitrogen, oxygen and sulfur atoms; or a condensed heterocyclic group resulting from fusion of a benzene or cyclohexene ring to the heterocyclic group, each of which may be substituted by 1 to 3 substituents described above.

Specifically,

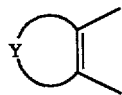

is preferably a benzene ring or a 5- or 6-membered hetero-monocyclic group containing one hetero atom, or a condensed heterocyclic group resulting from fusion of a benzene or cyclohexene ring with this heterocyclic ring. These benzene ring, hetero-monocyclic group and condensed heterocyclic ring may preferably contain 1 to 2 substituents described above.

In general formula [I], Cpr represents a cyclopropyl group which may have a substituent.

Specific examples of such a substituent are the same as those described in the above formula

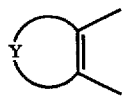

In general formula [I],

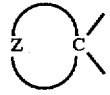

is a norbornylidene, a bicyclo[3.3.1]nonylidene or adamantylidene group which may have a substituent. The norbornylidene group is represented by the following formula

The bicyclo[3.3.1]nonylidene group is represented by the following formula

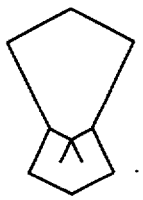

The adamantylidene group is represented by the following formula

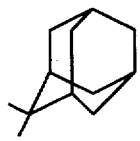

The above formulae show the skeletal structures of the norbornylidene group, the bicyclo[3.3.1]nonylidene group and the adamantylidene group having no substituent. One or more hydrogen atoms in the above formulae may be substituted by a substituent. The types and number of substituents and the substitution positions may be selected according to the purpose and utility. When the norbornylidene, bicyclo [3.3.1]nonylidene or adamantylidene group has a plurality of substituents, they may be of the same or different kinds.

Examples of the substituents for the norbornylidene, bicyclo[3.3.1]nonylidene or adamantylidene group include a hydroxyl group; alkylamino groups having 1 to 4 carbon atoms such as methylamino and diethylamino groups; alkoxy groups having 1 to 4 carbon atoms such as methoxy, ethoxy and tertbutoxy groups; aralkoxy groups having 7 to 15 carbon atoms such as a benzyloxy group; aryloxy groups having 6 to 14 carbon atoms such as phenoxy and 1-naphthoxy groups; lower alkyl groups having 1 to 4 carbon atoms such as methyl, ethyl and t-butyl groups; halogen atoms such as fluorine, chlorine and bromine atoms; a cyano group; a carboxyl group; alkoxycarbonyl groups having 2 to 10 carbon atoms such as an ethoxycarbonyl group; halogenated alkyl groups having 1 to 2 carbon atoms such as a trifluoromethyl group; a nitro group, aryl groups having 6 to 10 carbon atoms such as phenyl and tolyl groups; and aralkyl groups having 7 to 9 carbon atoms such as phenylethyl and phenylpropyl groups.

The halogen atoms, hydroxyl group, alkyl groups having 1 to 4 carbon atoms, alkoxy groups having 1 to 4 carbon atoms, alkoxycarbonyl groups having 2 to 10 carbon atoms, aralkyl groups having 7 to 9 carbon atoms and aryl groups having 6 to 10 carbon atoms are preferred.

In general formula [I] in this invention, X represents an oxygen atom (—O—), the group >N—$R_{11}$, the group >N—$A_1$—$B_1$—$(A_2)_m$—$(B_2)_n$—$R_{12}$, the group >N—$A_3$—$A_4$ or the group >N—$A_3R_{13}$.

Preferably, in general formula [I],

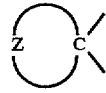

is a norboynylidene group, a bicyclo[3.3.1]nonylidene group or an adamantylidene group which may have a substituent, and X is the group >N—$A_1$—$B_1$—$(A_2)_m$—$(B_2)_n$—$R_{12}$, the group >N—$A_3$—$A_4$ or the group >N—$A_3$—$R_{13}$, especially the group >N—$A_3$—$R_{13}$ or the group >N—$A_1$—$B_1$—$(A_2)_m$—$(B_2)_n$—$R_{12}$.

Preferably, in general formula [I], X is the group >N—A$_1$—B$_1$—(A$_2$)$_m$—(B$_2$)$_n$—R$_{12}$ and R$_{12}$ is a naphthyl or naphthylalkyl group, or X is the group >N—A$_3$—A$_4$, the number of atoms in the main chain interposed between the naphthyl group and the imide group >N— is 3 to 7 because it leads to a compound having durable photochromism.

Now, the definitions of R$_{11}$, R$_{12}$, R$_{13}$, A$_1$, A$_2$, A$_3$, A$_4$, B$_1$, B$_2$, m and n in X will be described.

R$_{11}$ represents a hydrogen atom, an alkyl group having 1 to 20 carbon atoms, or an aryl group having 6 to 10 carbon atoms. Examples of the alkyl group are methyl, ethyl, n-, iso- or tert-butyl, pentyl, hexyl, octyl and decyl groups. Those having 1 to 10 carbon atoms are preferred. Examples of the aryl group are phenyl, tolyl and naphthyl groups.

A$_1$ and A$_2$ may be identical or different, and each may represent an alkylene group having 1 to 10 carbon atoms, an alkylidene group having 2 to 10 carbon atoms, a cycloalkylene group having 3 to 10 carbon atoms, or an alkylcycloalkanediyl group having 6 to 10 carbon atoms. Specific examples of the alkylene groups are methylene, ethylene, propylene, butylene, trimethylene, tetramethylene and 2,2-dimethyltrimethylene groups. Specific examples of the alkylidene groups are ethylidene, propylidene and isopropylidene groups. A cyclohexylene group may be cited as the example of the cycloalkylene groups. Examples of the alkylcycloalkanediyl groups are

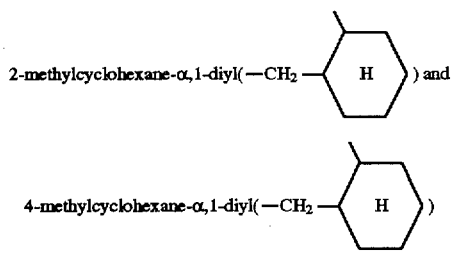

groups. The alkylene groups having 1 to 6 carbon atoms, the alkylidene groups having 2 to 6 carbon atoms, the cycloalkylene groups having 3 to 6 carbon atoms, and the alkylcycloalkanediyl groups having 6 to 7 carbon atoms are preferred as A$_1$ and A$_2$.

B$_1$ and B$_2$ may be identical or different, and each is selected from the following seven bridging groups.

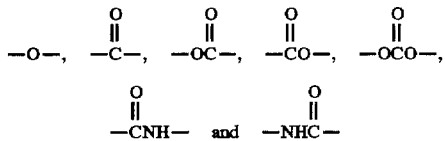

m and n, independently from each other, represent 0 or 1. When they represent 0, —(A$_2$)$_m$— or —(B$_2$)$_n$ means a bond. When m is 0, n is also 0.

R$_{12}$ represents an alkyl group having 1 to 10 carbon atoms, a naphthyl group, or a naphthylalkyl group having 1 to 4 carbon atoms in the alkyl moiety. The alkyl group having 1 to 10 carbon atoms may be substituted by 1 to 3 atoms or groups selected from the class consisting of halogen atoms, a cyano group and a nitro group. The naphthyl and naphthylalkyl groups may be substituted by 1 to 3 atoms or groups selected from the class consisting of halogen atoms, a cyano group, a nitro group, alkylamino groups having 1 to 3 carbon atoms, alkyl groups having 1 to 3 carbon atoms and alkoxy groups having 1 to 3 carbon atoms. Examples of the alkyl groups having 1 to 10 carbon atoms may be the same as those given with regard to the alkyl groups for R$_{12}$. Examples of the naphthylalkyl group are naphthylmethyl, naphthylethyl, naphthylpropyl and naphthylbutyl groups.

A$_3$ represents an alkylene group having 1 to 10 carbon atoms, an alkylidene group having 2 to 10 carbon atoms, a cycloalkylene group having 3 to 10 carbon atoms, or an alkylcycloalkanediyl group having 6 to 10 carbon atoms. Specific examples of the alkylene, alkylidene, cycloalkylene and alkylcycloalkanediyl groups may be the same as those given with regard to A$_1$ and A$_2$ above.

A$_4$ represents a naphthyl group which may be substituted by 1 to 3 atoms or groups selected from the class consisting of halogen atoms, cyano groups, nitro groups, alkylamino groups having 1 to 3 carbon atoms, alkyl groups having 1 to 3 carbon atoms and alkoxy groups having 1 to 3 carbon atoms.

R$_{13}$ represents a halogen atom, a cyano group or a nitro group.

In the definitions of R$_{12}$, R$_{13}$ and A$_4$, the halogen atom may be, for example, fluorine, chlorine or bromine.

In this invention, preferred examples of the compound represented by the general formula [I] are as follows.

(1)  4-cyclopropyl-6,7-dihydrdo-N-methoxycarbonylmethylspirobenzo[5,6-b]thiophenedicarboxyimido-7,7'-bicyclo[2.2.1]heptane (2)  N-cyanomethyl-4-cyclopropyl-6,7-dihydridospirobenzo[5,6-b]thiophenedicarboxyimido-7,7'-bicyclo[2.2.1]heptane (3)g  2-bromo-4-cyclopropyl-6,7-dihydrido-N-(β-naphtylethyl)spirobenzo[5,6-b]thiophenedicarboxyimido-7'9'-bicyclo[3.3.1]nonane (4)  2-bromo-4-cyclopropyl-6,7-dihydridospirobenzo[5,6-b]thiophenedicarboxyanhydride-7,2'-tricyclo[3.1.1$^{3.7}$]decane (5)  4-cyclopropyl-6,7-dihydrido-2-methyl-N-nitromethylspirobenzo[5,6-b]thiophenedicarboxyimide-7,7'-bicyclo[2.2.1]heptane (6)  4-(2"-methylcyclopropyl)-6,7-dihydrido-N-methylcarbonylmethyl-2-phenylspirobenzo[5,6-b]thiophenedicarboxyimido-7,7'-bicyclo[2,2,1]heptane (7)  3,4-dihydro-5,7-dimethoxy-N-(O-naphtylmethyl)-1-(2",3"-tetramethylcyclopropyl)spirophthalenedicarboxyimido-4,7'-bicyclo[2.2.1]heptane (8)  N-cyanomethyl-6,7-dihydro-4-(2-phenoxycyclopropyl)spirobenzo[6,5-b]furancarboxyimido-7,7'-bicyclo[2.2.1]heptane (9)  2-bromo-4-(2",3"-dichloromethyl)-6,7-dihydro-N-isobutoxycarbonylmethylspirobenzo[5,6-b]thiophenecarboxyimide-7,9'-bicyclo[3.3.1]nonane

(10)  6-cyclopropyl-8,9-dihydrospirodibenzo-[5,6-b:d]thiophenecarboxyanhydride-9,7'-bicyclo-[2.2.1]heptane

(11)  4-cyclopropyl-6,7'-1,2-dimethylspiroindolecarboxyanhydride-7,9'-bicyclo[3.3.1]nonane

(12)  2-bromo-4-cyclopropyl-3',3'-dimethylspirobenzo[5,6-b]thiophenecarboxyimido-7,9'-bicyclo[3.3.1]nonane

(13)  2-bromo-7-cyclopropyl-4,5-dihydro-N-methylcarboxymethylspirobenzo[5,6-b]thiophenecarboxyimido-4,2-tricyclo[3.3.1.1$^{3.7}$]decane

(14)  1,2,3,4,8,9-hexahydro-N-(α-naphtylpentyl)-6(2"-methylcyclopropyl)spirodibenzo[5,6-b:d]thiophenecarboxyimido-9,2'-tricyclo[3.3.1.1$^{3.7}$]-decane

(15) 4-cyclopropyl-6,7-dihydrido-2-nitrospirobenzo[5,6-b]thiophenedicarboxyanhydride-7,2'-tricyclo[3.3.1.1³,⁷]decane The compound of the general formula [I] generally exists as a pale yellow solid at room temperature, and can generally be identified by the following procedures (a) to (c).

(a) The types and number of protons existing in the molecule can be determined by measuring the proton nuclear magnetic resonance spectrum ($^1$H-NMR) of the compound. Specifically, in the $^1$H-NMR spectrum, there appears a peak based on aromatic protons near δ7–8 ppm, a broad peak based on protons derived from the cyclopropyl, adamantylidene, bicyclo[3.3.1]nonylidene or norbornylidene group near δ1.2–2.5 ppm. By comparing the δ peak intensities of these peaks, the number of protons of the bonding groups can be determined.

(b) By elemental analysts, the weight percentages of carbon, hydrogen, nitrogen, sulfur and halogen can be determined. The weight percent of oxygen can be calculated by subtracting the total weight percentage of the elements from 100. Accordingly, the composition of the product can be determined.

(c) The types of carbons present in the molecule can be determined by measuring the $^{13}$C-nuclear magnetic resonance spectrum of the compound. There appear a peak derived from carbons of the cyclopropyl, adamentylidene, bicyclo[3.3.1]nonylidene or norbornylidene group near δ27–52 ppm, a peak based on the carbons of the aromatic hydrocarbon group or the unsaturated heterocyclic group near δ110–150 ppm, and a peak based on the carbon of >C=O near δ160–170 ppm.

The compound of general formula [I] may be produced by any manufacturing process, and is not limited by the type of manufacturing process. Preferred typical processes are described below without any intention of limiting the invention thereby.

Process A

A process for producing a compound represented by the following general formula [I]

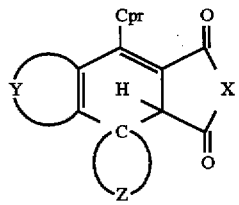

wherein

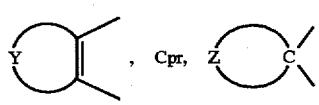

and

X are as defined hereinabove, which comprises cyclizing a compound represented by the following general formula [II]

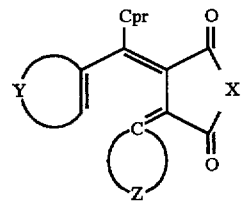

wherein

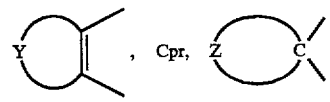

and

X are as defined with regard to general formula [I], or reacting the compound of general formula [II] with an amine compound represented by the following general formula [III-a], [III-b], [III-c] or [III-d]

| | |
|---|---|
| $H_2N$—$R_{11}$ | [III-a] |
| $H_2N$—$A_1$—$B_1$—$(A_2)_m$—$(B_2)_n$—$R_{12}$ | [III-b] |
| $H_2N$—$A_3$—$A_4$ | [III-c] |
| $H_2N$—$A_3$—$R_{13}$ | [III-d] | wherein
$R_{11}$, $R_{12}$, $R_{13}$, $A_1$, $A_2$, $A_3$, $A_4$, $B_1$, $B_2$, m and n are as defined above, and then cyclizing the reaction product.

A compound of general formula [I] in which X is an oxygen atom is obtained by cyclizing the acid anhydride of general formula [II] in process A. Compounds of general formula [I] containing an imide ring in which X is other than oxygen can be obtained by reacting the acid anhydride of general formula [II], with the amine compound of formula [III-a], [III-b], [III-c] or [III-d], and then cyclizing the resulting product.

The reaction in process A is carried out preferably in a solvent. The solvent may be an aprotic polar solvent such as N-methylpyrrolidone, dimethylformamide, tetrahydrofuran or 1,4-dioxane.

The direct cyclization of the acid anhydride of general formula [II] and the cyclization of the reaction product of the acid anhydride with the amine compound can be carried out under the same conditions. The cyclization is carried out, for example, by heating the compound to a temperature of 160° to 220° C., or carrying out this heating with ultraviolet irradiation, or by bringing the compound into contact with a Lewis acid catalyst. The Lewis acid catalyst may be a known compound such as $SnCl_4$, $TiCl_4$, $SbCl_5$ and $AlCl_3$. The amount of the Lewis acid used is not particularly restricted, but usually amounts of 0.001 to 1 mole per mole of the compound to be cyclized are preferred.

In the reaction of the acid anhydride of general formula [II] with the amine compound of general formula [III-a], [III-b], [III-c] or [III-d], the mole ratio of the acid anhydride to the amine compound can be varied over a wide range, but is generally from 1:10 to 10:1, preferably from 1:5 to 5:1. This reaction is carried out usually at a temperature of 25° to 160° C. for a period of 1 to 24 hours. After the reaction, the solvent is removed, and the product is dehydrated with a dehydrating agent such as acetyl chloride and acetic anhydride. By cyclizing the resulting compound under the conditions described above, the compound [I] of the invention can be obtained.

The acid anhydride of general formula [II] used as the starting material in process A can be obtained, for example, by condensing a carbonyl compound represented by the following general formula [II-a]

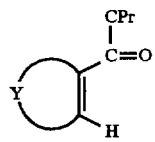  [II-a]

wherein

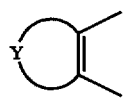

and
Cpr are as defined with regard to general formula [I], with a succinic diester derivative represented by the following general formula [II-b]

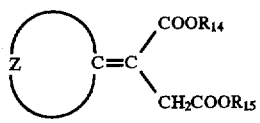  [II-b]

wherein

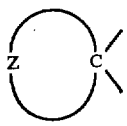

is as defined in general formula [I], and $R_{14}$ and $R_{15}$ are identical or different and represent an alkyl group having 1 to 6 carbon atoms,
and treating the resulting product in a manner described below.

The mole ratio of the carbonyl compound to the succinic diester derivative in the above condensation reaction may be varied over a wide range, and is generally from 1:10 to 10:1, preferably 1:5 to 5:1. The reaction is carried out at a temperature of 0° to 110° C. preferably 10° to 100° C. The reaction is suitably carried out in a solvent. The solvent is desirably an aprotic solvent such as benzene, diethyl ether, toluene and tetrahydrofuran.

Generally, the condensation is carried out in the presence of a condensing agent such as sodium hydride, potassium t-butoxide and sodium ethylate. The condensing agent may be used usually in an amount of 0.1 to 10 moles per mole of the carbonyl compound of general formula [II-a].

After the reaction, the resulting dicarboxylic acid diester is converted to the free dicarboxylic acid. This reaction is carried out by using known hydrolysis reaction conditions in the presence of bases. For example, the reaction is carried out at 0° to 80° C. using a 10% ethanolic aqueous solution of sodium hydroxide.

The resulting dicarboxylic acid can be converted to the acid anhydride of general formula [II] by known methods. Conversion into the acid anhydride may be carried out, for example, by using a well known reagent such as acetic anhydride or acetyl chloride.

Process B
A process for producing a compound represented by the following general formula [I]

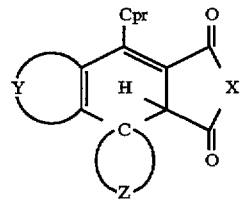  [I]

wherein

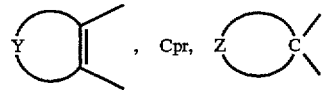

and
X are as defined with regard to general formula [I], provided that an oxygen atom is excluded from the above definition of X,
which comprises reacting an imide compound represented by the following general formula [IV]

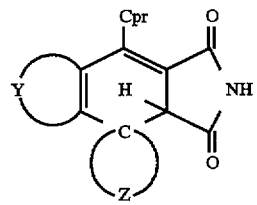  [IV]

wherein

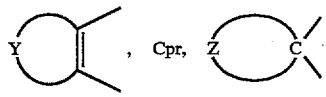

are as defined with regard to the general formula [I], with an alkali metal, and then reacting the product with a bromine compound represented by the following general formula [V-a], [V-b], [V-c] or [V-d]

| | |
|---|---|
| Br—$R_{11}$ | [V-a] |
| Br—$A_1$—$B_1$—$(A_2)_m$—$(B_2)_n$—$R_{12}$ | [V-b] |
| Br—$A_3$—$A_4$ | [V-c] |
| Br—$A_3$—$R_{13}$ | [V-d] | wherein
$R_{11}$, $R_{12}$, $R_{13}$, $A_1$, $A_2$, $A_3$, $A_4$, $B_1$, $B_2$, m and n are as defined with regard to the general formula [I].

Examples of the alkali metal used in process B are sodium, potassium, and lithium. The amount of the alkali metal to be reacted is generally 1.0 to 10 moles per mole of the compound of general formula [IV]. Preferably, the amount of the bromine compound of general formula [V-a], [V-b], [V-c] or [III-d] is generally 0.5 to 10 moles per mole of the compound [IV] obtained by reaction with the alkali.

The solvent used in this process may be any of those which are described above with regard to process A. Usually, the reaction temperature used may preferably be 0° to 100° C. The compound of general formula [I] of the invention can be obtained by the above processes A and B or by modifications of these processes.

The compound of general formula [I] has a photochromic action and excellent durability. By using it in combination with an ultraviolet stabilizer, the durability of the photochromic action of compound [I] can be further enhance. Accordingly, it is advantageous to use the compound [I] of the invention in combination with an ultraviolet stabilizer.

The ultraviolet stabilizer used for this purpose may be any of those known as additives to various plastics. If the durability of the compound [I] is considered, light extinguisher for oxygen in the singlet state and hindered amine light stabilizers can be suitably used as the ultraviolet stabilizer.

Examples of light extinguisher for oxygen in the singlet state which can be suitably used in this invention include a complex of $Ni^{2+}$ and an organic ligand, cobalt (III) tris-di-n-butyldithiocarbamate, iron (III) diisopropyldithiocarbamate and cobalt (II) diisopropyldithiocarbamate. The complex of $Ni^{2+}$ and an organic ligand is especially preferred. Examples of this complex are shown below.

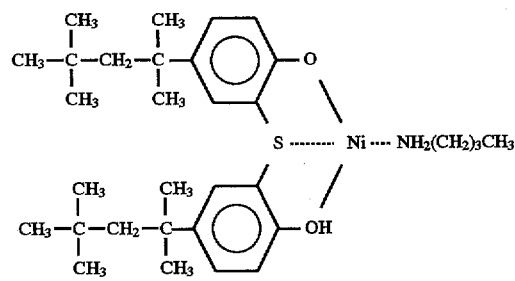

U-1

[2,2'-thiobis-4-(1,1,3,3-tetramethylbutyl)phenolate)butylamine]nickel

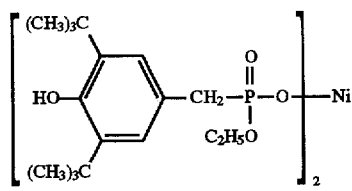

U-2

Nickel-bis[o-ethyl(3,5-di-tert-butyl-4-hydroxybenzyl)phosphonate

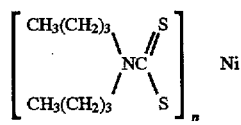

U-3

Nickel dibutyldithiocarbamate

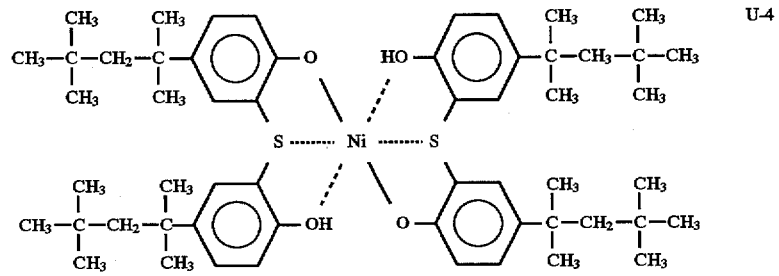

U-4 bis[2,2'-thiobis-4-(1,1,3,3-tetramethylbutyl)phenolate]nickel

There may also be cited Ni complexes sold by Ferro Corporation under the tradenames UV-Chek AM105, UV-Chek AM126 and UV-Chek AM205.

Specific examples of the hindered amine light stabilizers suitable as the ultraviolet stabilizer are given below.

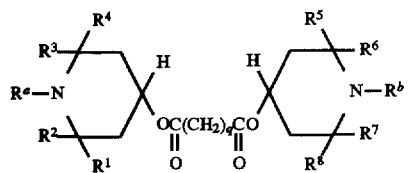
U-5
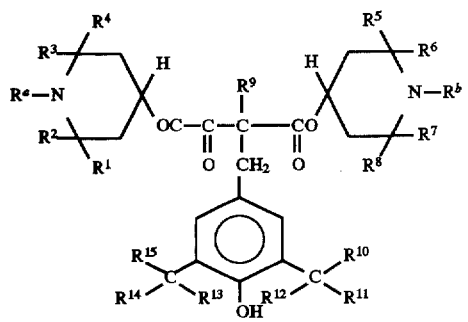
U-6
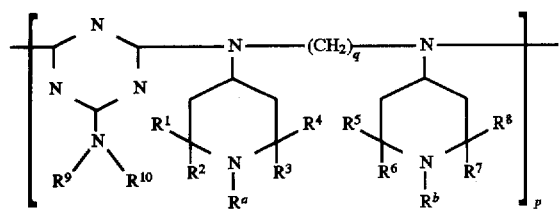
U-7
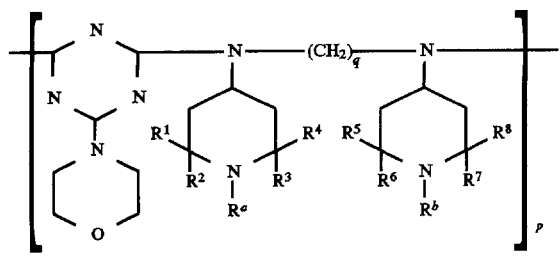
U-8
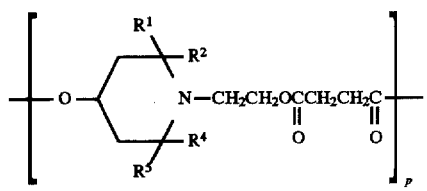
U-9
$(C_{26}H_{52}N_4)_p$
U-10
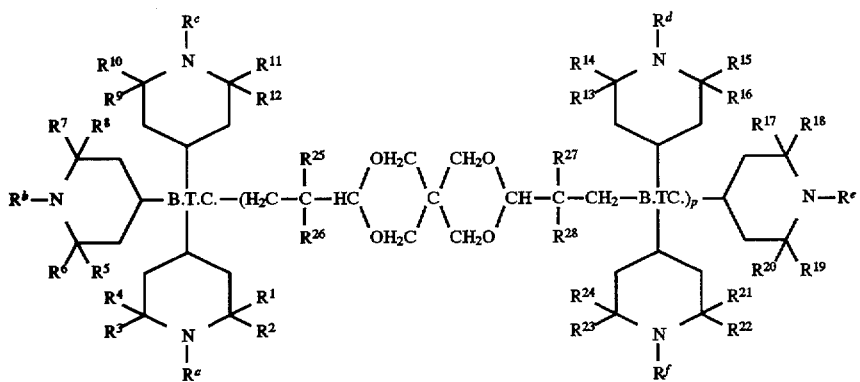
U-11

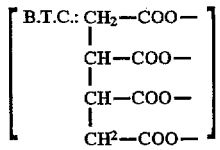

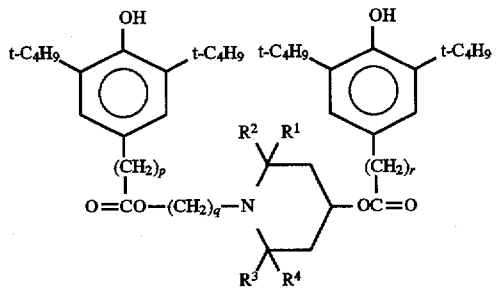

U-12

In the formulae, U-5 to U-12, $R^1$, $R^2$, $R^3$, $R^4$, $R^5$, $R^6$, $R^7$, $R^8$, $R^9$, $R^{10}$, $R^{11}$, $R^{12}$, $R^{13}$, $R_{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$ and $R^{28}$ represent an alkyl group, $R^a$, $R^b$, $R^c$, $R^d$, $R^e$ and $R^f$ represent a hydrogen atom or an alkyl group, and p, q and r are positive integers.

The alkyl groups In U-5 to U-12 are not particularly limited in the number of carbons. Generally, the alkyl groups preferably have 1 to 12 carbon atoms because of the ease of obtaining these compounds.

Sumisorb LS-2000 and LS-2001 (tradenames of Sumitomo Chemical Co., Ltd.) may also be cited as examples of the hindered amine light stabilizer.

Ultraviolet stabilizers of formulae U-1, U-3, U-5, U-6, U-8, U-9, U-11 and U-12 can be preferably used for increasing the durability of the photochromic actions of the compounds of general formula [I].

The mixing ratio of the compound of formula [I] and the ultraviolet stabilizer can be selected from a wide range. Generally, if the durability of a composition of the compound [I] and the ultraviolet stabilizer and the prevention of dissolution of the components, the proportion of the ultraviolet stabilizer is generally 0.01 to 10,000 parts by weight, more preferably 50 to 400 parts by weight, per 100 parts by weight of compound [I].

The compound of general formula [I] provided by this invention is well soluble in general organic solvents such as toluene, chloroform and tetrahydrofuran. When the compound [I] is dissolved in such a solvent, the solution has a reversible photochromic action such that it is almost colorless and transparent, and when sunlight or ultraviolet rays are irradiated onto it, it develops a color, and when the light is shut off, it rapidly attains the original colorless form. The compound of formula [I] also exhibits this photochromic action in a polymeric solid matrix with a reversing speed on the order of seconds. A high-molecular-weight polymer for forming such a polymeric material may be any polymer in which the compound [I] dispersible uniformly. The molecular weight of the high-molecular-weight polymer is selected from 500 to 500,000. Any of thermoplastic resins and thermosetting resins may be adopted as the polymer solid material.

The thermoplastic resins include, for example, polymethyl acrylate, polyethyl acrylate, polymethyl methacrylate, polyethyl methacrylate, polystyrene, polyacrylonitrile, polyvinyl alcohol, polyacrylamide, poly(2-hydroxyethylmethacrylate), polydimethylsiloxane and polycarbonate.

Dispersion of the compound represented by the general formula [I] of the present invention into a thermoplastic resin can be carried out by the synthesis of the thermoplastic, that is, the polymerization or melting and mixing the thermoplastic resin and the compound at temperature not less than a melting point of the thermoplastic resin.

The thermosetting resins include the polymers of radical polymeric multifunctional monomers which include, for example, polyvalent acrylate and polyvalent methacrylate compounds such as ethylene glycol diacrylate, diethylene glycol dimethacrylate, triethylene glycol dimethacrylate, tetraethylene glycol dimethacrylate, ethylene glycol bisglycidile methacrylate, bisphenol A dimethacrylate, 2,2-bis(4-methacryloyl oxyethoxy phenyl)propane, 2,2-bis(3,5-diboromo-4-methacryloyl oxyethoxy phenyl) propane; polyvalent allyl compounds such as diallyl phthalate, diallyl terephthalate, diallyl isophthalate, diallyl epoxy succinate, diallyl fumarate, diallyl chlorendate, diallyl hexaphthalate, diallyl carbonate, allyl diglycol carbanate, trimethylolpropane triallyl carbonate; polyvalent thioacrylate and polyvalent thiomethacrylate compounds such as 1,2-bis (methacryloylthio)ethane, bis(2-acryloyl thioethyl)ether, 1,4-bis(methacryloylthiomethyl)benzene; methacrylate or acrylate compounds such as glycidyl acrylate, glycidyl methacrylate, β-methylglycidyl methacrylate, β-methylglycidyl acrylate, bisphenol A-monoglycidylether methacrylate, 4-glycidyloxybutyl methacrylate, 3-(glycidyloxy-1-isopropyloxy)-2-hydroxypropyl acrylate, 3-(glycidyloxy-2-hydroxypropyloxy)-2-hydroxypropyl acrylate; and divinylbenzene. The thermosetting resins may also include, for example, copolymers of the radical polymeric multifunction monomers with radical polymeric monofunctional monomers including unsaturated carboxylic acids such as acrylic acid, methacrylic acid, maleic anhydride; acrylate and methacrylate compounds such as methyl acrylate, methyl methacrylate, benzyl methacrylate, phenyl methacrylate, 2-hydroxyethyl methacrylate; fumarate compounds such as diethyl fumarate, diphenyl fumarate; thioacrylate and thiomethacrylate compounds such as methyl thioacrylate, benzyl thioacrylate, benzyl thiomethacrylate; and vinyl compounds such as styrene, chlorostyrene, methylstyrene, vinylnaphthalene and bromostyrene. The thermosetting resins may further include addition copolymers of the above-mentioned radical polymeric multifunctional monomers with polyvalent thiol compounds such as ethanedithiol, propanethiol, hexanodithiol, pentaerythritol tetrakisthioglycolate, di(2-mercaptoethyl)ether; and addition copolymers of polyvalent isocyanate compounds such as diphenylethane diisocyanate, xylene diisocyanate, p-phenylene diisocyanate with polyvalent alcohol compounds such as ethylene glycol, trimethylolpropane, pentaerythritol, bisphenol A on the above-mentioned polyvalent thiol compounds.

Dispersion of the compound of the general formula [I] into the thermosetting resin may be generally carried out by mixing the starting monomers of the thermosetting resin with the compound of the general formula [I] and thereafter polymerizing them.

The amount of the compound [I] to be dispersed in the above high-molecular polymer is generally 0.001 to 70 parts by weight, preferably 0.005 to 30 parts by weight, especially preferably 0.1 to 15 parts by weight, per 100 parts by weight of the high-molecular polymer. When the ultraviolet stabilizer is used by mixing it with the high-molecular polymer, its amount may be within the range of the mixing proportion with respect to the compound [I] described above.

The photochromic action of the compound of general formula [I] has much higher durability than known fulgimide compounds.

Accordingly, the compounds of this invention can be broadly utilized as a photochromic material. For example, they can be utilized in various recording materials superseding silver salt photographic materials, for example, in memory materials, printing photographic materials, recording materials for a cathode ray tube, photographic materials for laser and photographic materials for holography. The photochromic material containing the compound of this invention can also be utilized as a photochromic lens material, an optical filter material, a display material, an actinometer or a decorative material. For example, a photochromic lens may be produced by any method which can give uniform light adjusting properties. Specifically, a polymer film in which the photochromic compound of this invention is uniformly dispersed in sandwiched between lenses. Alternatively, a photochromic lens may be produced by dissolving the compound of the invention in a silicone oil, impregnating the solution in the surface of a lens at 150° to 200° C. over 10 to 60 minutes, and coating the surface with a curable substance. It is also possible to coat the above polymer film on the surface of a lens and coating the surface with a curable substance to provide a photochromic lens. A photochromic lens may also be produced by dispersing the compound of the invention in monomers capable of forming an organic lens, and then polymerizing and curing the monomeric mixture.

When the photochromic compound is used as an photochromic lens, a color such as grey or brown is preferred. Since such a single photochromic compound cannot give such a color, a method of mixing two or more photochromic compounds may be adopted. The compound of general formula [I] is generally colored in orange to blue. When it is mixed with the chromene compound which is colored in yellow to orange, an intermediate color such as grey and brown may be obtained. Generally, fulgide compound has a poor durability of photochromic properties as compared with chromene compound, and changes may occur in color with the lapse of time. For this reason, a mixed color of the fulgide compound and the chromene compound changes with time. However, in accordance with this invention, by increasing the durability of photochromism of the fulgide compound, it is made close to the durability of the chromene compound, and a divergence in color with the lapse of time can be minimized.

The chromene compound preferably used in admixture with the compound of general formula [I] to obtain an intermediate color may be represented by formula [V].

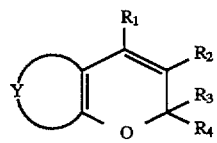

wherein $R_1$, $R_2$, $R_3$ and $R_4$ are the same or different, and each represents a hydrogen atom, an alkyl group, an aryl group, a substitution amino group or a saturated heterocyclic group, $R_3$ and $R_4$ may together form a ring, and the group

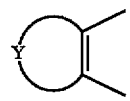

is a divalent aromatic hydrocarbon group or a divalent unsaturated heterocyclic group each of which may have a substituent.

Examples of the alkyl and aryl groups represented by $R_1$, $R_2$, $R_3$ and $R_4$ in formula [V] may be the alkyl and aryl groups described above with regard to formula [I]. Examples of the substituted amino group may be amino groups whose at least one hydrogen atom is substituted by the aforesaid alkyl or aryl group. Examples of the saturated heterocyclic group include monovalent groups derived from 5- to 6-membered rings containing 1 to 2 ring-constituting atoms such as nitrogen atoms, oxygen atoms and sulfur atoms such as a pyrrolidine group, an imidazolidine ring, a piperidine ring, a piperazine ring and a morphorine ring.

Examples of the ring formed by $R_3$ and $R_4$ in formula [V] include a norbornylidene group and a bicyclo[3.3.1] nonylidene group.

The aromatic hydrocarbon group or the unsaturated heterocyclic group represented by

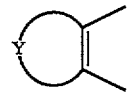

in the formula [IV] may be the same as those show in formula [I]. Substituents of these groups are not particularly limited. Examples of the substituents include halogen atoms such as chlorine, bromine and iodine, alkyl groups having 1 to 20 carbon atoms such as methyl group and an ethyl group, alkoxy groups having 1 to 20 carbon atoms such as a methoxy group and an ethoxy group, aryl groups having 6 to 10 carbon atoms such as a phenyl group, a tolyl group and a xylyl group, amino groups, a nitro group and a cyano group.

Examples of the chromene compounds preferably used in this invention include those of formula [V] in which $R_1$ and $R_2$ are both hydrogen atoms, and $R_3$ and $R_4$ are same or different alkyl groups having 1 to 4 carbon atoms, or together may form a bicyclo[3.3.1]nonylidene group or a norbornylidene group,

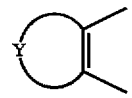

is a naphthalene ring which may be substituted by an alkyl group having 1 to 20 carbon atoms or an alkoxy group having 1 to 20 carbon atoms.

The chromene compounds that can be used preferably in this invention are listed below.

(1) Spiro(norbornane-2,2'-(2H)benzo(h)-chromene)
(2) Spiro(bicyclo[3.3.1]nonane-9,2'-(2H)benzo(f)-chromene)
(3) 7'-methoxyspiro(bicyclo[3.3.1]nonane-9,2'-(2H)benzo(f)-chromene)
(4) 7'-methoxyspiro(norbornane-2,2'-(2H)benzo(f)-chromene)
(5) 2,2-dimethyl-7-octoxy(2H)benzo(f)-chromene
(6) 4'-methylspiro[bicyclo[3.3.1]nonane-9,2'-[2H]benzo[f]chromene]
(7) 3'-methylspiro[norbornane-2,2'-[2H]benzo-[f]chromene]
(8) Spiro[tricyclo[3.3.1.1$^{3,7}$]decane-2,2'-[2H]benzo[h]chromene
(9) 4'-piperidinospiro[bicyclo[3.3.1]nonane-9,2'-[2H]benzo[h]chromene]
(10) 2,2-dimethyl-6-octadecyl[2H]benzo-[h]chromene
(11) spiro[norbornane-2,2'-[2H]naphtho[1,2-h]chromene]
(12) 2,2-dimethyl-7-(ethylthiohexyl)oxy[2H]-benzo[h]chromene
(13) 6-chloro-2,2-dimethyl-7-(dipropylphosphonohexyl)oxy[2H]benzo[h]chromene
(14) 2,2-dimethyl[2H]pyrido[2,3-h]chromene
(15) 7-methoxy-2,2-dimethyl[2H]benzo[h]chromene
(16) 7-(diethylaminooctyl)-2,2-dimethyl-[2H]benzo[h]chromene The mixing ratio of the compound of formula [I] and the chromene compound can be selected from a wide range. Generally, the proportion of the chromene compound is generally 0.01 to 10,000 parts by weight, more preferably 0.05 to 200 parts by weight, per 100 parts by weight of the compound [I].

Compared to the conventional compounds, the compound of general formula [I] in this invention shows markedly improved durability by the effect of the cyclopropyl group, and is longer in maximum absorption wavelength of color form. Further, the compound of general formula [I] wherein X is an oxygen atom is quite increased in color density in comparison to the conventional compounds.

Figure 1:
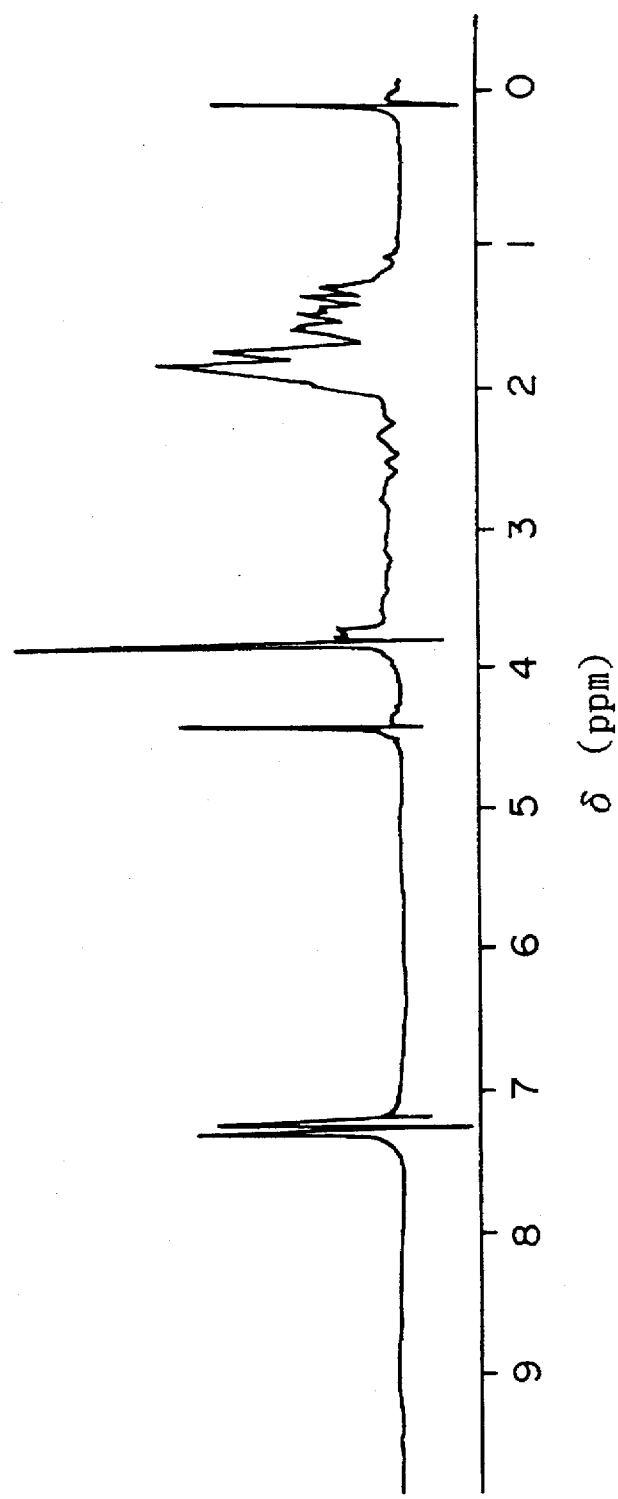
FIG. 1 is the proton nuclear magnetic resonance spectrum of the product obtained in Example 1.

The following examples illustrate the present invention in greater detail without limiting the invention thereby.

In the examples, the following ultraviolet stabilizers were used.

Cyasorb UV1084 (tradename; product of American Cyanamid Co.)

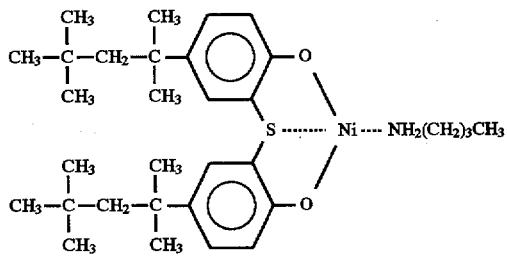

Irganostab 2002 (tradename; produced by Ciba-Geigy Co.)

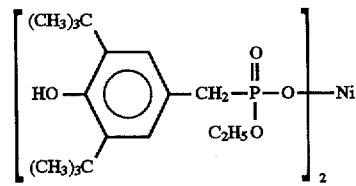

Rylex NBC (tradename; product of E. I. du Pont de Nemours & Co.)

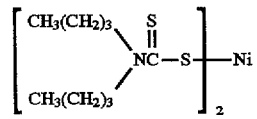

UV-Chek AM101 (tradename; produced by Ferro Corporation)

-continued
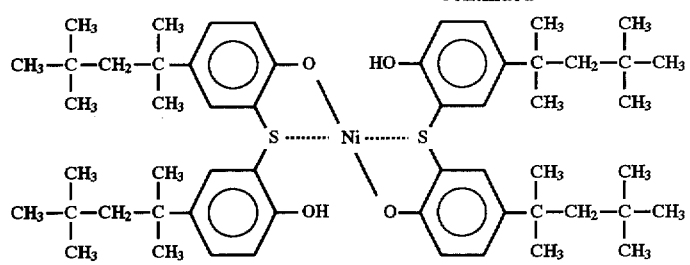
UV-Chek AM105 (tradename; produced by Ferro Corporation)
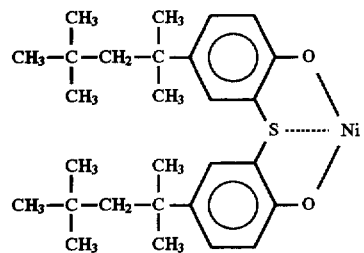
Tinuvin 765 (tradename; produced by Ciba-Geigy Co.)
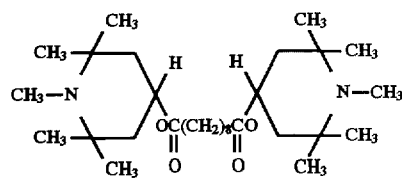
Tinuvin 144 (tradename; produced by Ciba-Geigy Co.)
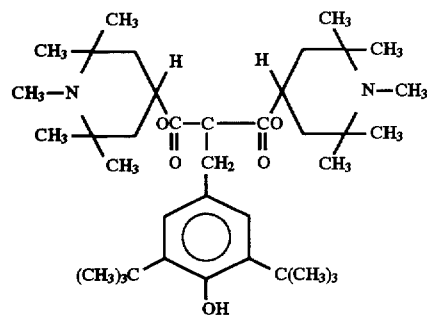
Chimasorb 944 (tradename; produced by Ciba-Geigy Co.)
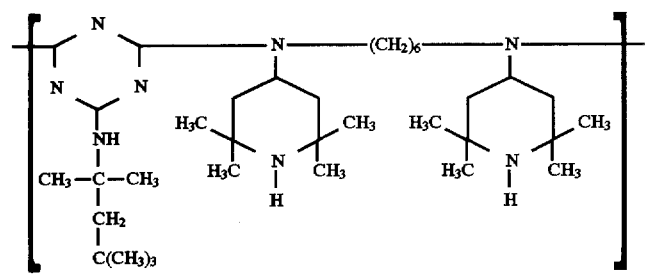
Cyasorb 3346 (tradename; produced by American Cyanamid Co.)

-continued

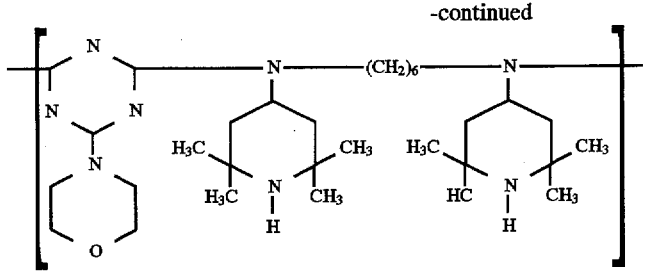

Tinuvin 622 (tradename; produced by Ciba-Geigy Co.)

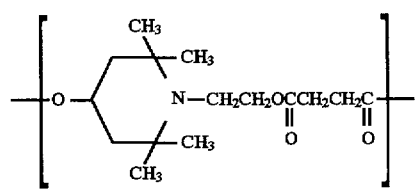

Spinuvex A-36 (tradename; produced by Borg Warner Corp.)
$C_{26}H_{52}N_5$

LA-63 (tradename; produced by Adeca-Agas Corp.)

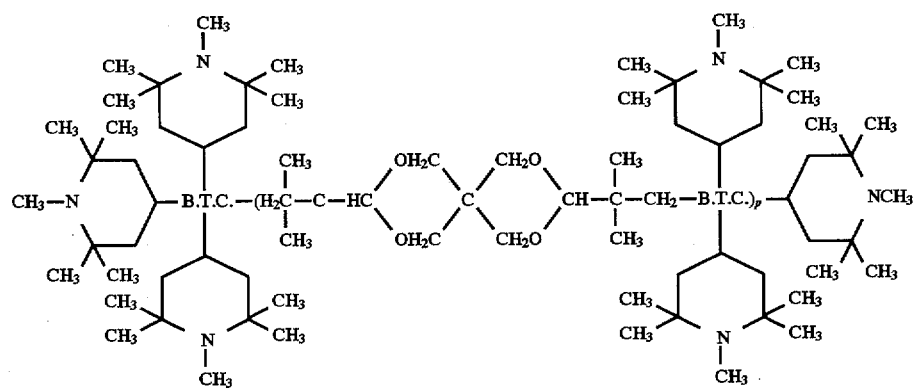

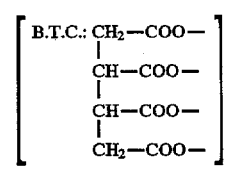

LS-2626 (tradename; produced by Sankyo Co.)

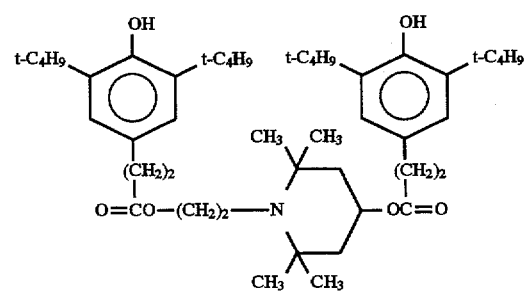

In the Example, the following chromene compound were mentioned.

(1) Spiro(norbornane-2,2'-(2H)benzo(h)-chromene)
(2) 7'-methoxyspiro(bicyclo[3.3.1]nonane-9,2'-(2H)benzo(f)-chromene)
(3) 4'-methylspiro[bicyclo[3.3.1]nonane-9,2'-[2H]benzo[f]chromene]
(4) 3'-methylspiro[norbornane-2,2'-[2H]benzo-[f]chromene]
(5) 2,2-dimethyl-7-octoxy[2H]benzo[h]chromene

EXAMPLE 1

3.3 g (0.01 mole) of cyclopropyl-3-thienylmethylidene-7-norbornylidene succinic anhydride of the following formula

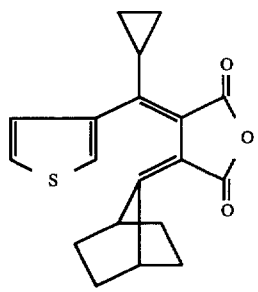

and 17.8 g (0.02 mole) of glycine methyl ester of the following formula

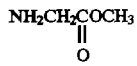

were dissolved in toluene, and the solution was heated at 50° C. for 2 hours in a nitrogen atmosphere. After the reaction, the solvent was removed, and the residue was dissolved in acetyl chloride. The solution was refluxed for 1 hour to cyclize the reaction product. The resulting compound was refluxed for 6 hours in o-dichlorobenzene to convert it into a compound of formula [I]. This compound was purified by chromatography on a silica gel column using benzene and ether as an eluent. Recrystallization from chloroform and hexane gave pale yellow needles in a yield of 23%. The elemental analysis values of this compound were C 66.52%, H 5.86%, N 3.49%, O 16.3% and S 8.11%, which well agreed with the calculated values for $C_{20}H_{21}O_4NS$ (C 66.48%, H 5.83%, N 3.52%, O 16.1% and S 8.07%). The proton nuclear magnetic resonance spectrum of the resulting compound was taken and shown in FIG. 1. The proton nuclear magnetic resonance spectrum of the resulting compound showed a peak of 2H based on aromatic protons near δ7.0–8.0 ppm, a peak of 3H based on the methyl protons of the

bond near δ3.7 ppm, a peak of 15H based on the protons of the cyclopropyl group and the 7-norbornylidene group at δ1.2–2.5 ppm, and a peak of 3H based on the 1–5 shifted proton and the >N—CH$_2$— bond at δ3–5 ppm.

The $^{13}$C-NMR spectrum of the resulting product was measured. It showed a peak based on the carbons of the 7-norbornylidene group and the carbon of the methylene chain at δ27–70 ppm, a peak based on the carbon of the cyclopropyl group near δ9.7 ppm, and a peak based on the carbons of the thiophene ring near δ110–160 ppm, and a peak based on the carbon of the >C=O bond near δ160–170 ppm.

From the above results, the isolated products was determined to be a compound of the following structural formula

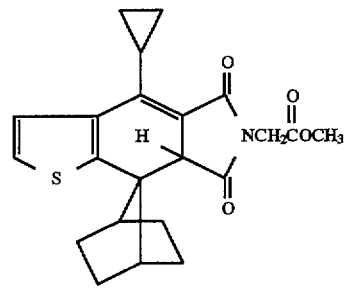

EXAMPLE 2

3.0 g (0.01 mole) of a compound of the following formula

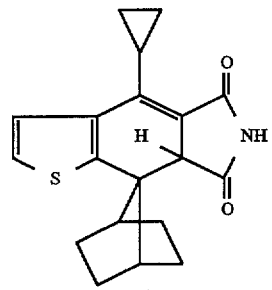

was dissolved in tetrahydrofuran, and then reacted with 1 g of metallic potassium at room temperature to give 3.0 g of potassium imide of the following formula

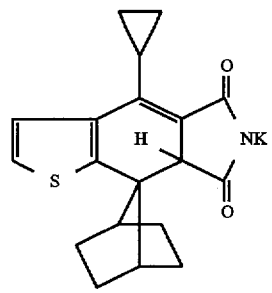

This compound was reacted with 1.2 g (0.01 mole) of bromoacetonitrile BrCH$_2$CN in dimethylformamide to give a fulgimide compound shown below. This compound was purified by chromatography on silica gel using chloroform and hexane as an eluent and was obtained in a field of 52% as pale yellow crystals by recrystallization from hexane. This compound had the following elemental analysis values: C 69.25%, H 5.55%, N 7.71%, O 8.75% and S 8.90% . These values well agreed with the calculated values for $C_{19}H_{18}N_2O_2S$ (C 69.21%, H 5.53%, N 7.69%, O 8.78% and S 8.8%). The proton nuclear magnetic resonance spectrum of the resulting compound was measured. The spectrum showed a peak of 2H based on aromatic protons of thiophene ring near δ7.0–7.5 ppm, a peak of 2H based on the protons of >N—CH$_2$CN bond near δ4.5 ppm, a peak of 1H based on the 1–5 shifted proton near δ3.7 ppm, and a peak of 12H based on the protons of the cyclopropyl group and the 7-norbornylidene group at δ1.3–2.5 ppm.

The $^{13}$C-NMR of the resulting compound was also measured. The spectrum showed a peak based on the carbons of the 7-norbornylidene group near δ27–70 ppm, a peak based on the cyclopropyl carbon near δ10.2 ppm, a peak based on the carbons of the thiophene ring near δ110–160 ppm, and a peak based on the carbon of >C=O bond near δ160–170 ppm.

From the above results, this isolated product was determined to be a fulgimide compound of the following structural formula

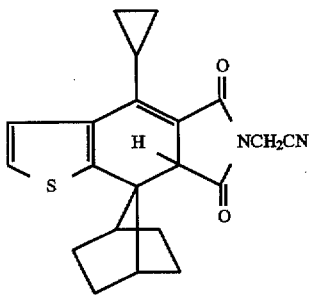

EXAMPLE 3

4.3 g (0.01 mole) of the following compound

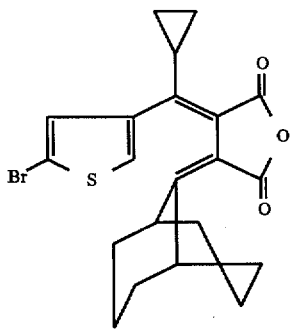

and 3.5 g (0.02 mole) of 2-naphthylethylamine of the following formula

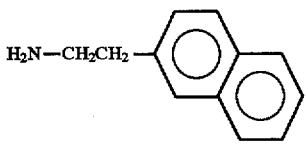

were dissolved in toluene, and heated at 50° C. for 2 hours in an atmosphere of nitrogen. After the reaction, the solvent was removed, and the residue was dissolved in acetyl chloride, and refluxed for 1 hour to cyclize the product obtained above. The resulting compound was refluxed for 6 hours in o-dichlorobenzene to form a compound shown below. The compound was purified by chromatography on silica gel using benzene and ether as an eluent. By recrystallization from chloroform and hexane, it was obtained as yellow needles in a yield of 25%. The elemental analysis values of this compound were C 67.61%, H 5.52%, Br 13.65%, N 2.39%, O 5.50% and S 5.41%, which well agreed with the calculated values for $C_{31}H_{30}BrNO_2S$ (C 67.57%, H 5.5%, Br 13.62%, N 2.39%, O 5.46% and S 5.47%). The proton nuclear magnetic resonance spectrum of the resulting compound was measured. The spectrum showed a peak of 8H based on aromatic protons near δ7.0–8.0 ppm, a peak of 3H based on the 1–5 shifted proton and based on the protons of >N—CH$_2$— near δ3.8 ppm, and a peak of 23H based on the protons of the —CH2— bond and the protons of the cyclopropyl group and the bicyclo[3.3.1]9-nonylidene group near δ1.3–2.5 ppm.

The $^{13}$C-NMR spectrum of the resulting product was also measured. It showed a peak based on the carbons of the bicyclo[3.3.1]9-nonylidene group and the carbon of the methylene chain at δ27–52 ppm, a peak based on the carbon of the cyclopropyl group near δ9.70 ppm, a peak based on the carbons of the naphthalene ring and the carbons of the thiophene ring near δ110–160 ppm, and a peak based on the carbon of the >C=O bond near δ160–170 ppm.

From the above results, the isolated products was determined to be a fulgimide compound of the following structural formula

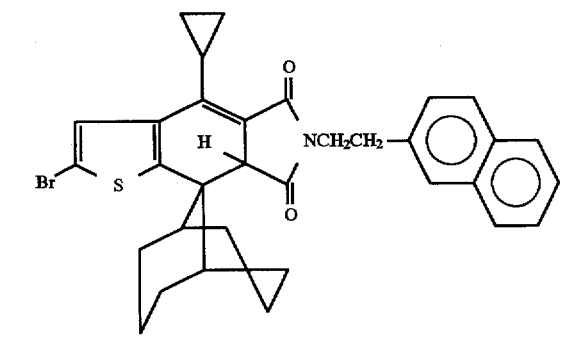

EXAMPLE 4

A fulgimide compound of the following structural formula was obtained by repeating Example 3 except that NH3 was used instead of 2-naphthylethylamine.

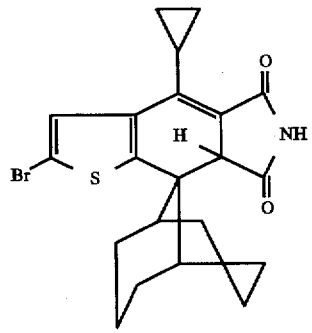

6.5 g (0.015 mole) of this compound was dissolved in tetrahydrofuran, and reacted with metallic sodium at room temperature to give 5.4 g of an imide sodium of the following formula

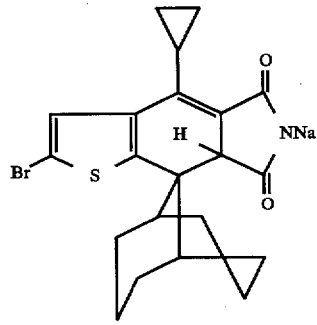

This compound was reacted with 2 g (0.01 mole) of 2-bromomethyl 2-naphthoxyacetate of the following formula

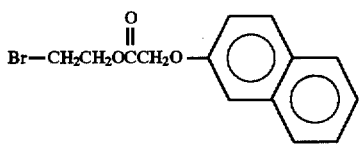

in dimethylformamide to give a fulgimide compound shown below. This compound was purified by chromatography on silica gel using chloroform and hexane as an eluent, and from hexane, it was obtained as yellow needles in a yield of 47%.

The resulting compound had elemental analysis values of C 63.67%, H 5.21%, Br 12.15%, N 2.15%, O 12.15% and S 4.90%, which well agreed with the calculated values for $C_{33}H_{31}BrNO_5S$ (C 63.63%, H 5.19%, Br 12.1%, N 2.12%, O 12.11% and S 4.85%).

The proton NMR spectrum of the resulting compound was measured. The spectrum showed a peak of 8H based on aromatic protons near δ7.0–8.0 ppm, a peak of 7H based on the protons of the —$CH_2$— bond and the 1–5 shifted proton near δ3.0–5.0 ppm, and a peak of 14H based on the cyclopropyl group and the bicyclo[3.3.1]9-nonylidene group at δ1.0–2.2 ppm.

The $^{13}$C-NMR spectrum of the resulting product was also measured. The spectrum showed a peak based on the carbons of the bicyclo[3.3.1]9-nonylidene group and the carbon of the methylene chain at δ27–52 ppm, a peak based on the carbon of the cyclopropyl group near δ9.7 ppm, a peak based on the carbon of the thiophene ring and the carbons of the naphthalene ring near δ110–160 ppm, and a peak based on the carbon of the >C=O bond near δ160–170 ppm.

From the above results, the isolated products was determined to be a fulgimide compound of the following structural formula

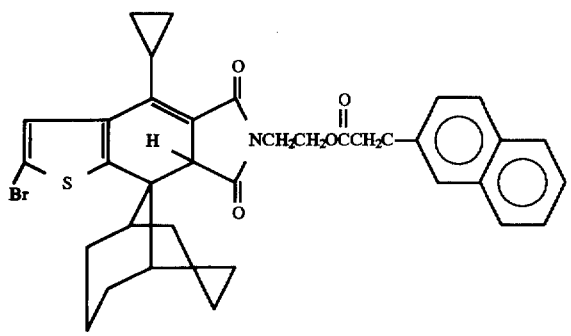

EXAMPLE 5

3.7 g (0.01 mole) of cyclopropyl-3-thienylmethylidene succinic anhydride of the following formula

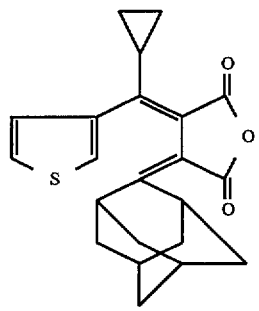

and 2.1 g (0.02 mole) of 2-naphthylethyl 2-aminobutyrate of the following formula

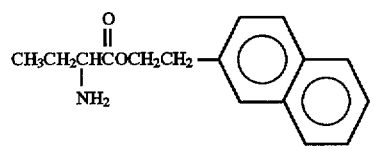

were dissolved in toluene, and heated at 50° C. for 2 hours in an atmosphere of nitrogen. After the reaction, the solvent was removed, and the residue was dissolved in acetyl chloride and refluxed for 1 hour to cyclize the above reaction product. The resulting compound was refluxed for 6 hours in o-chlorobenzene to form a fulgimide compound of the following structure. This compound was purified by chromatography on silica gel using benzene and ether as an eluent. By recrystallization from chloroform and hexane, it was obtained as yellow needles in a yield of 29%.

The elemental analysis values of the resulting compound were C 76.65%, H 5.00%, N 2.30%, O 10.75% and S 5.43%, which well agreed with the calculated values for $C_{33}H_{33}O_4NS$ (C 76.62%, H 4.91%, N 2.35%, O10.74% and S 5.38%).

The proton NMR spectrum of the resulting compound was measured. The spectrum showed a peak of 9H based on aromatic protons near δ7.0–8.0 ppm, a peak of 3H based on the protons of the methyl group in the —$CH_2CH_3$ bond at δ0.8–1.2 ppm, a peak of 12H based on protons of the —$CH_2$— bond and the cyclopropyl group and adamantylidene group at δ1.2–2.5 ppm, and a peak of 7H based on the 1–5 shifted proton and the —$CH_2$— bond at δ3–5 ppm.

The $^{13}$C-NMR spectrum of the resulting product was also measured. The spectrum showed a peak based on the carbons of the adamantylidene group and the carbon of the methylene group at δ27–52 ppm, a peak based on the carbon of the cyclopropyl group near δ9.7 ppm, a peak based on the carbons of the thiophene group and the carbons of the naphthyl group near δ110–160 ppm, and a peak based on the carbon of the >C=O bond near δ160–170 ppm.

From the above results, the isolated product was determined to be a fulgimide compound of the following structural formula

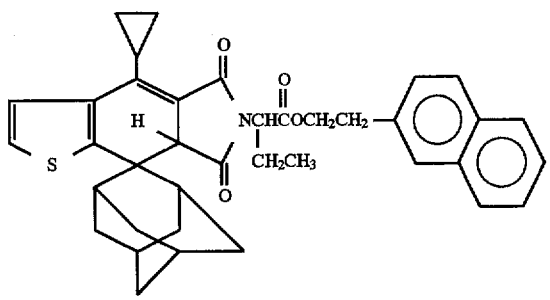

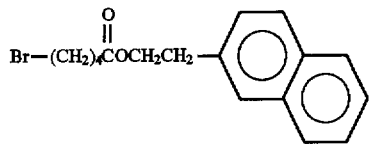

were reacted in dimethylformamide to give a fulgimide compound shown below. This compound was purified by chromatography on silica gel using chloroform and hexane as an eluent. By recrystallization from hexane, it was obtained as yellow crystals in a yield of 63%.

EXAMPLE 6

3.5 g (0.01 mole) of a fulgimide compound of the following formula

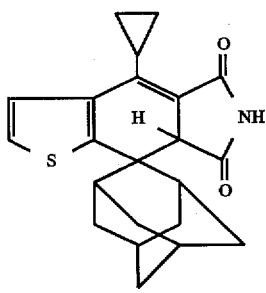

The elemental analysis values of the resulting compound were C 75.91%, H 5.35%, N 2.41%, O 10.91% and S 5.50%, which well agreed with the calculated values for $C_{34}H_{35}NO_4S$ (C 75.87%, H 5.33%, N 2.39%, O 10.93% and S 5.47%).

The proton NMR spectrum of the resulting compound was measured. The spectrum showed a peak of 9H based on aromatic protons near δ7.0–8.0 ppm, a peak of 2H based on the protons of the

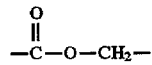

was dissolved in tetrahydrofuran, and reacted with 1 g of metallic potassium at room temperature to give 3.0 g of imide potassium of the following formula

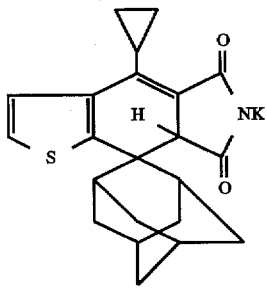

The resulting compound and 1.8 g (0.01 mole) of 2-naphthylethyl 5-bromovalerate of the following formula bond near δ4.4 ppm, a peak of 3H based on the 1–5 shifted proton and protons of the >N—CH$_2$— bond near δ3.7 ppm, a peak of 27H based on the protons of —CH$_2$— bond and the protons based on the cyclopropyl group and adamantylidene group at δ1.3–2.5 ppm.

The $^{13}$C-NMR spectrum of the resulting product was also measured. The spectrum showed a peak based on the carbons of the adamantylidene group and the carbon of the methylene chain at δ27–52 ppm, a peak based on the carbon of the cyclopropyl group near δ9.7 ppm, a peak based on the carbons of the thiophene group and the carbons of the naphthalene ring near δ110–160 ppm, and a peak based on the carbon of the >C=O bond near δ160–170 ppm.

From the above results, the isolated products was determined to be a fulgimide compound of the following structural formula

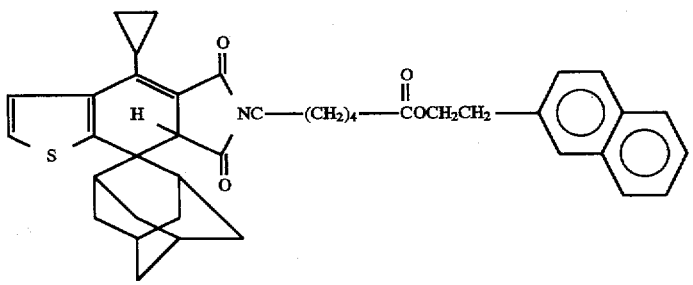

EXAMPLE 7

11.3 g (0.049 mole) of cyclopropyl-(5-bromo-3-thienyl) ketone and 19.6 g (0.084 mole) of diethyladamantylidene succinate of the following formula

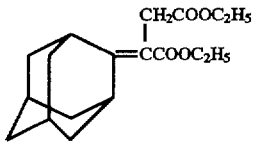

were dissolved in 200 cc of toluene to form a solution. The toluene solution was added dropwise over 3 hours in an atmosphere of nitrogen to a solution of 5 g of sodium hydride in 200 cc of toluene so that the temperature of the toluene solution became 0° C. or below. After the addition, the mixture was vigorously stirred for 10 hours while the liquid temperature was maintained at 0° C. or below. The mixture was hydrolyzed with an excessive amount of a 10% alcoholic aqueous solution of potassium hydroxide and acidified with hydrochloric acid. The resulting dicarboxylic acid was treated with 100 cc of acetyl chloride, and purified by chromatography on silica gel to give 12.8 g of fulgide compound of the following formula

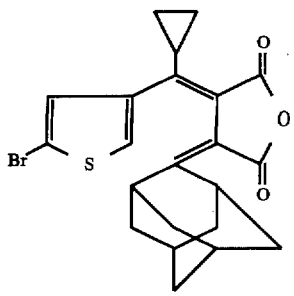

The resulting compound was refluxed in o-dichlorobenzene for 8 hours to rearrange it to a fulgide compound of the following formula

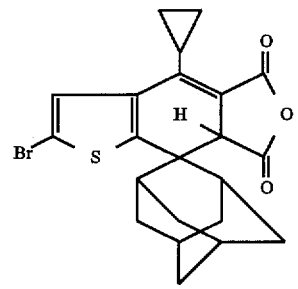

This compound was purified by chromatography on silica gel using benzene and ether as an eluent. By recrystallization from chloroform and hexane, it was obtained as yellow needles in a yield of 35%. The elemental analysis values of this compound were C 59.35%, H 4.79%, O 10.81%, S 7.25% and Br 18.01%, which well agreed with the calculated values for $C_{19}H_{19}O_3SBr$ (C 59.33%, H 4.75%, O 10.78%, S 7.20% and Br 17.94%).

The proton NMR spectrum of the resulting compound was measured. The spectrum showed a peak of 1H based on the proton of the thiophene ring near δ7.2 ppm, a peak of 1H based on the 1–5 shifted proton near δ4.0 ppm, and a broad peak of 19H based on the protons of the cyclopropyl group and the adamantylidene group near δ1.2–2.5 ppm.

The $^{13}C$-NMR spectrum of the resulting compound was also measured. It showed a peak based on the carbons of the bicyclo[3.3.1]9-nonylidene group near δ27–52 ppm, a peak based on the carbon of the cyclopropyl group near δ9.7 ppm, a peak based on the carbons of the thiophene ring near δ110–160 ppm, and a peak based on the carbon of the >C=O bond near δ160–170 ppm.

From the above results, the isolated products was identified as a compound of the above structural formula.

EXAMPLE 8

In the same way as in Examples 1 to 7, various compounds were synthesized from the starting materials shown in Tables 1 to 18. The yields of the products are also shown in Tables 1 to 18.

By the same elemental analysis, proton NMR spectrum analysis and $^{13}C$-NMR spectral analysis as in Examples 1 to 7, the resulting compounds were determined to have the structures shown in Tables 1 to 8.

The results of the elemental analysis are shown in Tables 19 to 21.

TABLE 1

| | Starting Material | Product | Yield |
|---|---|---|---|
| 1 | (structure) $H_2NCH_2NO_2$ | (structure) | 20 |

TABLE 1-continued

| | Starting Material | | Product | Yield |
|---|---|---|---|---|
| 2 | [structure: methoxy-benzothiophene with cyclopropyl-Cl and anhydride with norbornyl] | H₂NCH₂Cl | [structure: corresponding cyclized product with NCH₂Cl imide] | 15 |
| 3 | [structure: phenyl-thiophene with methyl-cyclopropyl and anhydride with norbornyl] | H₂NCH₂CCH₃ (with =O) | [structure: corresponding cyclized product with NCH₂COCH₃ imide] | 20 |

TABLE 2

| | Starting Material | | Product | Yield |
|---|---|---|---|---|
| 4 | [structure: nitro-thiophene with CF₃-cyclopropyl and anhydride with norbornyl] | H₂NCH₂C(=NOH)CH₃ | [structure: corresponding cyclized product with NCH₂C(=NOH)CH₃ imide] | 30 |
| 5 | [structure: furan with dimethyl-cyclopropyl and anhydride with chloro-norbornyl] | CH₃ H₂NCHCOCH₃ (with =O) | [structure: corresponding cyclized product with N(CH(CH₃)COCH₃) imide] | 23 |

TABLE 2-continued

| | Starting Material | | Product | Yield |
|---|---|---|---|---|
| 6 | [structure with Br, Br cyclopropyl, benzofuran, OCH₃] | $H_2NCH_2COCCH_2CH_2CN$ with CH₃, CH₃ groups | [product structure with Br, Br, OCH₃, NCH₂COCCH₂CH₂CN] | 25 |

TABLE 3

| | Starting Material | | Product | Yield |
|---|---|---|---|---|
| 7 | [structure with phenyl, cyclopropyl, thiophene, Cl, Cl] | $H_2NCH_2OCH_2CN$ | [product with phenyl, thiophene, Cl, Cl, NCH₂OCH₂CN] | 23 |
| 8 | [structure with SCH₃, cyclopropyl, N-methylpyrrole, CH₃] | $H_2NCH_2CH_2CCH_2CH_2CNCH_3$ with O and OH | [product with SCH₃, pyrrole, CH₃, NCH₂CH₂CCH₂CH₂CNCH₃] | 15 |
| 9 | [structure with F, F, F, F, F, benzofuran] | $H_2NCH_2OCH_2OCH_3$ | [product with F's, benzofuran, NCH₂OCH₂CH₂OCH₃] | 20 |

TABLE 4

| Starting Material | | Product | Yield |
|---|---|---|---|
| 10 [structure] | [structure of H₂NCCN reagent with CH₃ groups] | [structure] | 23 |
| 11 [structure] | [H₂NCH₂-naphthalene] | [structure] | 21 |
| 12 [structure] | [H₂NCH₂-naphthalene] | [structure] | 20 |

TABLE 5

| Starting Material | | Product | Yield |
|---|---|---|---|
| 13 [structure] | BrCH₂COCH₃ | [structure] | 30 |

TABLE 5-continued

| | Starting Material | | Product | Yield |
|---|---|---|---|---|
| 14 | [structure] | [structure: BrCH₂OCCH₂-naphthyl] | [structure] | 50 |
| 15 | [structure] | BrCH₂CN | [structure] | 12 |

TABLE 6

| | Starting Material | | Product | Yield |
|---|---|---|---|---|
| 16 | [structure] | H₂NCH₂COCH₂CH(CH₃)₂ | [structure] | 20 |
| 17 | [structure] | H₂NCHCH₂OCOCH₂NO₂ (with C₂H₅) | [structure] | 17 |

TABLE 6-continued
| | Starting Material | | Product | Yield |
|---|---|---|---|---|
| 18 | 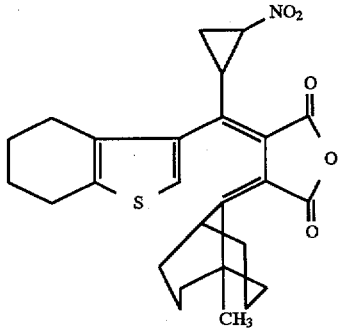 | $\underset{H_2NCHCN}{C_2H_5}$ | 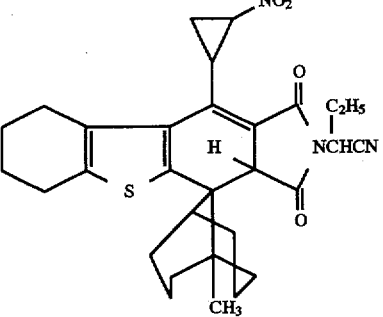 | 23 |
TABLE 7
| | Starting Material | | Product | Yield |
|---|---|---|---|---|
| 19 | 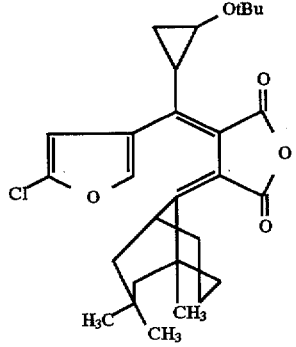 | $\underset{H_2NCHCOCH_3}{\underset{\parallel}{CH_3}}$ $\phantom{H_2NCHCOCH_3}O$ | 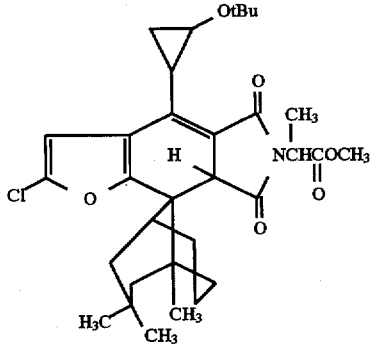 | 20 |
| 20 | 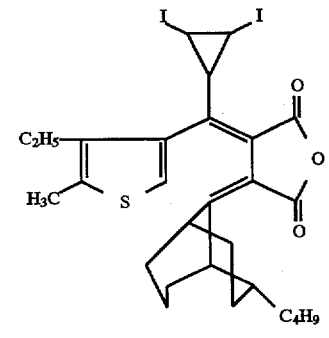 | 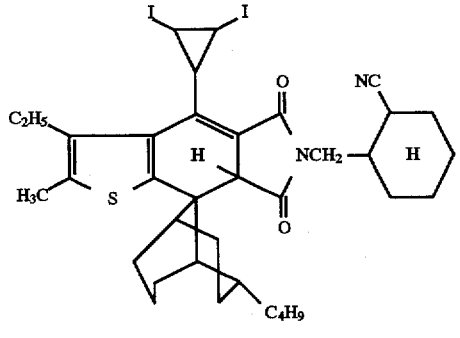 | 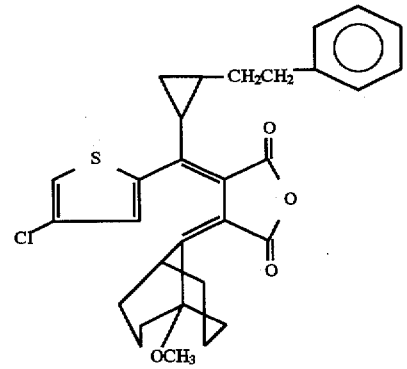 | 19 |
| 21 | 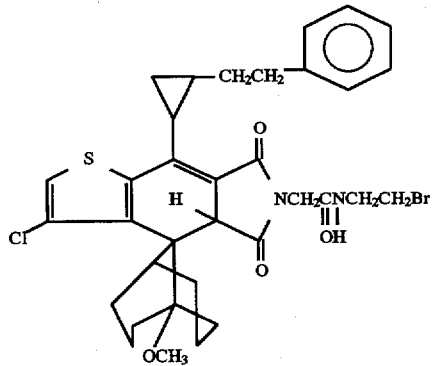 | $\underset{\underset{OH}{\parallel}}{H_2NCH_2CNCH_2CH_2Br}$ |  | 25 |

TABLE 8

| Starting Material | | Product | Yield |
|---|---|---|---|
| 22 | (structure with OH, cyclopropyl, CH₃O, anhydride, Cl) + H₂N-C₆H₁₀-NO₂ | (naphthalene-derived imide product with cyclopropyl, OH, CH₃O, H₃CO, Cl, N-cyclohexyl-NO₂) | 25 |
| 23 | (furan-fused structure with C₃H₇-cyclopropyl, H₃CO, imide NH) + CH₃-BrCHCCH₃(=O) | (furan-fused product with C₃H₇-cyclopropyl, H₃CO, N-CH(CH₃)C(=O)CH₃) | 27 |
| 24 | (diphenylcyclopropyl-thiophene fused imide NH with H₃CO-C₆H₄) + BrCH₂OCOC₂H₅ | (same core with N-CH₂OCOC₂H₅) | 31 |

TABLE 9

| Start Material | | Product | Yield |
|---|---|---|---|
| 25 | (pyrrole-fused cyclopropyl imide NH, N-phenyl, gem-diCH₃) + BrCH₂CH₂OCOCH₂-naphthyl | (same core with N-CH₂CH₂OCOCH₂-naphthyl) | 50 |

TABLE 9-continued

| | Start Material | | Product | Yield |
|---|---|---|---|---|
| 26 | [structure: cyclohexane-fused thiophene with cyclopropyl, spiro ring, dicarboximide NH] | BrCH₂CH₂–naphthyl | [structure: same core with NCH₂CH₂-naphthyl imide] | 45 |
| 27 | [structure: thiophene with CH₃S and CH₃, cyclopropyl-N(CH₃)₂, spiro ring, dicarboximide NH] | 2-bromo-cyclohexyl-NC | [structure: same core with N-(2-cyano-cyclohexyl) imide] | 37 |

TABLE 10

| | Starting Material | | Product | Yield |
|---|---|---|---|---|
| 28 | [structure: thiophene with 4-methoxyphenyl, cyclopropyl, dichloro-adamantyl spiro, anhydride] | CH₃—H₂NCHCOCH₃ (with C=O) | [structure: same core with N-(CH(CH₃)COCH₃) imide] | 18 |
| 29 | [structure: thiophene with CH₃O, CH₃, OC₂H₅-cyclopropyl, adamantyl spiro, anhydride] | C₂H₅—H₂NCHCN | [structure: same core with N-CH(C₂H₅)CN imide] | 25 |

TABLE 10-continued
| | Starting Material | | Product | Yield |
|---|---|---|---|---|
| 30 | 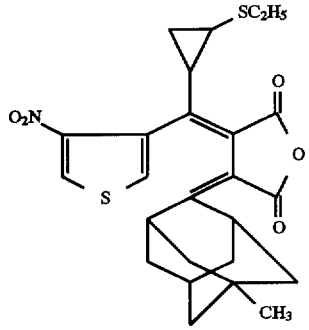 | $H_2NCHCH_2OCOCH_2NO_2$ with $C_2H_5$ substituent | 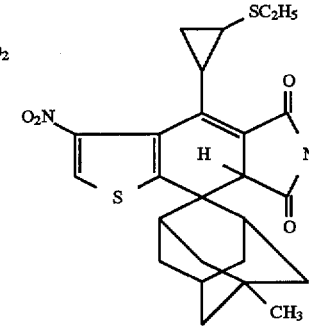 | 20 |
TABLE 11
| | Starting Material | | Product | Yield |
|---|---|---|---|---|
| 31 | 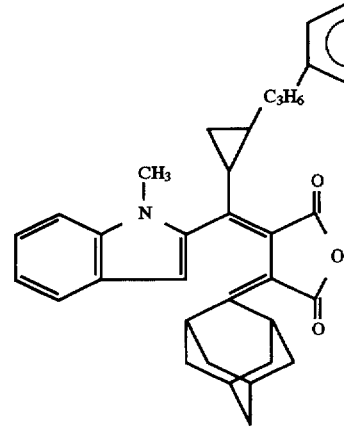 | $H_2NCH_2\underset{CH_3}{\overset{CH_3}{C}}CH_2CH_2O\underset{O}{\overset{\|}{C}}CH_2Br$ | 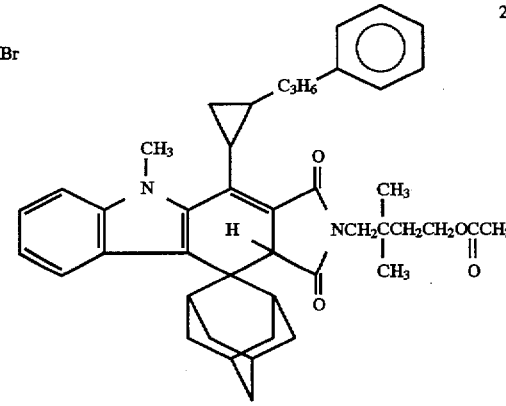 | 23 |
| 32 | 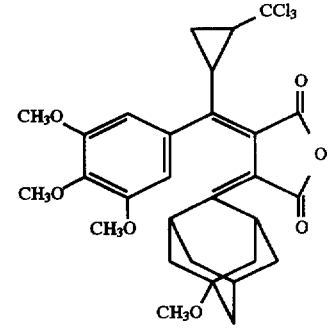 | $H_2NCH_2\underset{OH}{\overset{\|\|}{C}}NCH_2CH_2Br$ | 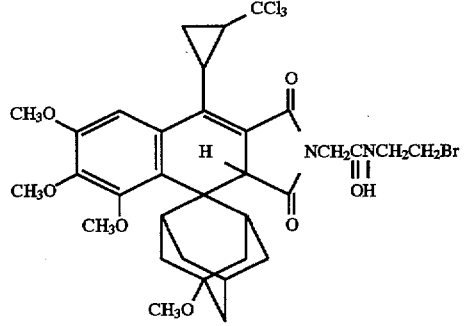 | 25 |
| 33 | 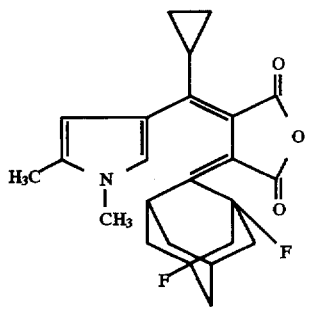 | $H_2N\text{—}\bigcirc\text{—}NO_2$ | 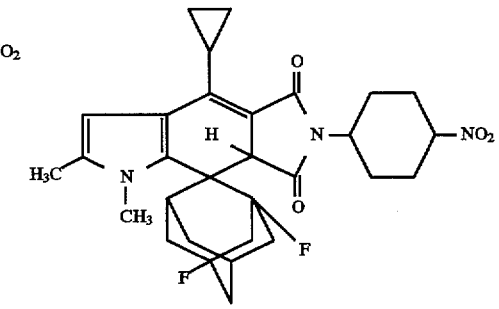 | 32 |

TABLE 12

| | Starting Material | | Product | Yield |
|---|---|---|---|---|
| 34 | [structure] | BrCH₂OCOC₂H₅ | [structure] | 32 |
| 35 | [structure] | BrCH₂OCCH₃ | [structure] | 35 |
| 36 | [structure] | BrCH₂CF₂ | [structure] | 27 |

TABLE 13

| | Starting Material | | Product | Yield |
|---|---|---|---|---|
| 37 | [structure] | BrCH₂COCH₂CH₂CN | [structure] | 39 |

TABLE 13-continued

| | Starting Material | | Product | Yield |
|---|---|---|---|---|
| 38 | [structure: 6-methoxy-8-methoxy naphthalene with cyclopropyl, spiro adamantane, dicarboximide NH] | BrCHCCH$_2$NO$_2$ with C$_2$H$_5$ and C=O | [structure: product with NCHCCH$_2$NO$_2$, C$_2$H$_5$ substituent] | 45 |
| 39 | [structure: tetrahydrobenzothiophene fused ring with cyclopropyl, spiro adamantane, dicarboximide NH] | BrCH$_2$CNCH$_2$CH$_2$Cl with ∥ OH | [structure: product with NCH$_2$CNCH$_2$CH$_2$Cl, OH substituent] | 30 |

TABLE 14

| Starting Material | Product | Yield |
|---|---|---|
| 40 (structure with NH imide, cyclopropyl, thiophene-NO₂, adamantane) + Br-(CH₂)₃-naphthyl-N(CH₃)₂ | N-(CH₂)₃-naphthyl-N(CH₃)₂ imide product | 55 |
| 41 (structure with NH imide, CH₃, cyclopropyl, thiophene-cyclohexyl, adamantane) + Br-(CH₂)₅-naphthyl | N-(CH₂)₅-naphthyl imide product | 60 |
| 42 (thiophene-benzofused cyclopropyl ketone structure) + CH₂—COOC₂H₅ / COOC₂H₅ bicyclic | anhydride product with cyclopropyl, thiophene-phenyl, bicyclic | 23 |

TABLE 15

| | Starting Material | Product | Yield |
|---|---|---|---|
| 43 | (structure) | (structure) | 33 |
| 44 | (structure) | (structure) | 35 |
| 45 | (structure) | (structure) | 17 |

TABLE 16

| | Starting Material | Product | Yield |
|---|---|---|---|
| 46 | (structure) | (structure) | 7 |

TABLE 16-continued

| | Starting Material | Product | Yield |
|---|---|---|---|
| 47 | (tetrahydrobenzothiophene with C(O)-cyclopropyl) | =CCOOC$_2$H$_5$, CH$_2$COOC$_2$H$_5$ (bicyclic alkene) → spiro anhydride product | 12 |
| 48 | (2-ethoxy-thiophene with C(O)-cyclopropyl, C$_2$H$_5$O-S-) | =CCOOC$_2$H$_5$, CH$_2$COOC$_2$H$_5$ (bicyclic alkene) → spiro anhydride product | 25 |

TABLE 17

| | Starting Material | Product | Yield |
|---|---|---|---|
| 49 | (5-bromofuran with C(O)-cyclopropyl, Br-O-) | =CCOOC$_2$H$_5$, CH$_2$COOC$_2$H$_5$ (methyl-substituted bicyclic alkene, CH$_3$) → spiro anhydride product | 15 |
| 50 | (N-ethylindole with C(O)-cyclopropyl, N-C$_2$H$_5$) | =CCOOC$_2$H$_5$, CH$_2$COOC$_2$H$_5$ (methyladamantylidene, CH$_3$) → spiro anhydride product | 12 |

TABLE 17-continued

| | Starting Material | | Product | Yield |
|---|---|---|---|---|
| 51 | 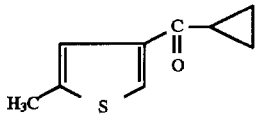 | 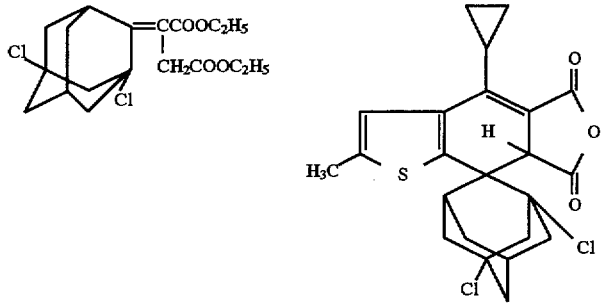 | 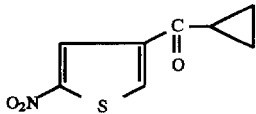 | 25 |

TABLE 18

| | Starting Material | | Product | Yield |
|---|---|---|---|---|
| 52 | 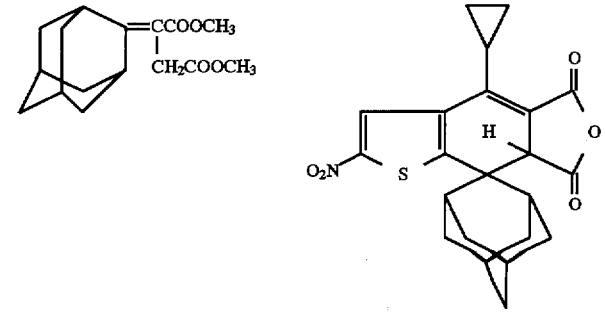 | | | 27 |

TABLE 19

| | Elemental analysis value (%) | | | | | | | | | | | | |
|---|---|---|---|---|---|---|---|---|---|---|---|---|---|
| | Determined value | | | | | | Calculated value | | | | | | |
| No. | C | H | N | O | S | Others | C | H | N | O | S | Others | $^1$H-NMR spectrum (ppm) |
| 1 | 63.37 | 5.61 | 7.06 | 16.11 | 8.11 | | 63.3 | 5.56 | 7.03 | 16.06 | 8.05 | | δ7.2:1H, δ3.0~5.0:3H, δ1.2~2.7:18H |
| 2 | 61.31 | 4.81 | 2.91 | 9.82 | 6.51 | Cl 14.9 | 61.23 | 4.73 | 2.86 | 9.79 | 6.54 | Cl 14.87 | δ7.0~8.0:3H, δ3.0~5.0:6H, δ1.2~2.7:15H |
| 3 | 73.91 | 6.25 | 3.01 | 10.22 | 6.85 | | 73.86 | 6.2 | 2.97 | 10.18 | 6.8 | | δ7.0~8.0:6H, δ3.0~5.0:6H, δ1.2~2.7:17H |
| 4 | 54.25 | 4.41 | 8.21 | 15.65 | 6.32 | F 11.21 | 54.22 | 4.35 | 8.25 | 15.7 | 6.29 | F 11.19 | δ7.3:1H, δ3.0~5.0:7H, δ1.2~2.7:14H |
| 5 | 65.45 | 6.17 | 3.11 | 17.45 | | Cl 7.91 | 65.43 | 6.15 | 3.05 | 17.43 | | Cl 7.94 | δ7.0~8.0:2H, δ3.0~5.0:5H, δ1.2~2.7:21H |
| 6 | 54.91 | 4.65 | 4.03 | 13.73 | | Br 22.85 | 54.8 | 4.74 | 3.99 | 13.69 | | Br 22.78 | δ7.0~8.0:4H, δ3.0~5.0:6H, δ1.2~2.7:23H |
| 7 | 62.15 | 4.51 | 5.19 | 8.91 | 5.95 | Cl 13.51 | 62.11 | 4.47 | 5.17 | 8.86 | 5.92 | Cl 13.46 | δ7.0~8.0:7H, δ3.0~5.0:5H, δ1.2~2.7:12H |
| 8 | 65.53 | 7.15 | 8.05 | 12.19 | 6.17 | | 66.51 | 7.12 | 8.02 | 12.22 | 6.12 | | δ7.0~8.0:2H, δ3.0~5.0:7H, δ1.2~2.7:28H |
| 9 | 56.57 | 3.82 | 2.49 | 13.9 | | F 23.21 | 56.55 | 3.87 | 2.44 | 13.95 | | F 2.19 | δ7.0~8.0:4H, δ4.0~5.0:10H, δ1.2~2.7:8H |
| 10 | 75.29 | 8.25 | 4.95 | 11.4 | | | 75.24 | 8.3 | 5.01 | 11.45 | | | δ7.0~8.0:2H, δ3.0~5.0:7H, δ1.2~2.7:37H |
| 11 | 79.3 | 7.15 | 2.45 | 11.08 | | | 79.27 | 7.18 | 2.43 | 11.12 | | | δ7.0~8.0:9H, δ3.0~5.0:9H, δ1.2~2.7:23H |
| 12 | 77.11 | 5.81 | 2.63 | 8.89 | 5.92 | | 77.04 | 5.73 | 2.57 | 8.8 | 5.88 | | δ7.0~8.0:11H, δ3.0~5.0:6H, δ1.2~2.7:14H |
| 13 | 69.25 | 6.12 | 3.70 | 20.95 | | | 69.28 | 6.08 | 3.67 | 20.97 | | | δ7.0~8.0:2H, δ3.0~5.0:6H, δ1.2~2.7:15H |
| 14 | 72.53 | 5.65 | 6.62 | 15.19 | | | 72.48 | 5.6 | 6.67 | 15.24 | | | δ7.0~8.0:14H, δ3.0~5.0:7H, δ1.2~2.7:14H |
| 15 | 73.65 | 5.52 | 6.31 | 14.58 | | | 73.62 | 5.49 | 6.36 | 14.53 | | | δ7.0~8.0:7H, δ3.0~5.0:3H, δ1.2~2.7:14H |
| 16 | 53.91 | 5.33 | 2.19 | 9.95 | 4.92 | Cl 11.32 Br 12.39 | 53.96 | 5.31 | 2.17 | 9.92 | 4.97 | Cl 11.3 Br 12.38 | δ7.2:1H, δ3.0~5.0:9H, δ1.2~2.7:24H |
| 17 | 66.02 | 6.12 | 9.37 | 18.71 | | | 65.99 | 6.04 | 9.33 | 18.65 | | | δ7.0~8.0:4H, δ3.0~5.0:9H, δ1.2~2.7:23H |
| 18 | 67.55 | 6.59 | 7.91 | 12.04 | 6.05 | | 67.52 | 6.61 | 7.87 | 11.99 | 6.01 | | δ3.0~5.0:2H, δ1.2~2.7:33H |
| 19 | 67.11 | 7.34 | 2.49 | 16.71 | | Cl 6.41 | 67.06 | 7.39 | 2.44 | 16.75 | | Cl 6.36 | δ7.2:1H, δ3.0~5.0:5H, δ1.2~2.7:36H |
| 20 | 52.45 | 5.65 | 3.45 | 3.91 | 3.93 | I 30.75 | 52.43 | 5.62 | 3.4 | 3.88 | 3.89 | I 30.78 | δ3.0~5.0:3H, δ1.2~2.7:43H |
| 21 | 59.45 | 5.51 | 4.13 | 9.33 | 4.71 | Cl 5.35 Br 11.65 | 59.43 | 5.57 | 4.08 | 9.31 | 4.67 | Cl 5.31 Br 11.63 | δ7.0~8.0:6H, δ3.0~5.0:7H, δ1.2~2.7:25H |
| 22 | 63.55 | 6.37 | 4.81 | 19.13 | | Cl 6.25 | 63.53 | 6.36 | 4.78 | 19.11 | | Cl 6.22 | δ7.0~8.0:2H, δ3.0~5.0:8H, δ1.2~2.7:27H |
| 23 | 72.65 | 7.79 | 2.95 | 16.72 | | | 72.62 | 7.78 | 2.92 | 16.68 | | | δ7.2:1H, δ3.0~5.0:5H, δ1.2~2.7:31H |
| 24 | 74.05 | 6.11 | 1.99 | 13.47 | 4.51 | | 74.03 | 6.07 | 1.96 | 13.45 | 4.49 | | δ7.0~8.0:15H, δ3.0~5.0:8H, δ1.2~2.7:20H |
| 25 | 77.41 | 6.85 | 4.15 | 11.67 | | | 77.39 | 6.79 | 4.1 | 11.72 | | | δ7.0~8.0:14H, δ3.0~5.0:7H, δ1.2~2.7:25H |

TABLE 20

| No. | \multicolumn{6}{c}{Determined value} | \multicolumn{6}{c}{Calculated value} | ¹H-NMR spectrum (ppm) |
|---|---|---|---|---|---|---|---|---|---|---|---|---|---|
| | C | H | N | O | S | Others | C | H | N | O | S | Others | |
| 26 | 79.14 | 7.09 | 2.53 | 5.72 | 5.73 | | 79.11 | 7 | 2.49 | 5.7 | 5.71 | | δ7.0~8.0:7H, δ3.0~5.0:3H, δ1.2~2.7:29H |
| 27 | 68.21 | 7.35 | 7.51 | 5.72 | 11.32 | | 68.17 | 7.33 | 7.45 | 5.68 | 11.37 | | δ7.2:1H, δ3.7:1H, δ1.2~2.7:39H |
| 28 | 63.11 | 5.31 | 2.27 | 12.75 | 5.13 Cl | 11.63 | 63.06 | 5.29 | 2.23 | 12.73 | 5.1 Cl | 11.6 | δ7.0~8.0:5H, δ3.0~5.0:8H, δ1.2~2.7:20H |
| 29 | 69.25 | 7.03 | 5.43 | 12.34 | 6.23 | | 69.2 | 6.97 | 5.38 | 12.29 | 6.16 | | δ3.0~5.0:7H, δ1.2~2.7:29H |
| 30 | 56.47 | 5.73 | 6.39 | 21.87 | 9.81 | | 56.43 | 5.65 | 6.37 | 21.83 | 9.72 | | δ7.2:1H, δ3.0~5.0:6H, δ1.2~2.7:30H |
| 31 | 71.2 | 6.92 | 3.65 | 8.47 | | Br 10.65 | 70.3 | 6.84 | 3.73 | 8.51 | | Br 10.63 | δ7.0~8.0:9H, δ3.0~5.0:8H, δ1.2~2.7:34H |
| 32 | 51.92 | 4.97 | 3.72 | 14.73 | Cl 14.35 Br 10.47 | | 51.88 | 5.01 | 3.67 | 14.66 | Cl 14.32 Br 10.46 | | δ7.0:1H, δ3.0~5.0:16H, δ1.2~2.7:21H |
| 33 | 66.82 | 6.57 | 7.83 | 11.89 | F 7.12 | | 66.77 | 6.54 | 7.79 | 11.86 | F 7.04 | | δ7.2:1H, δ3.0~5.0:4H, δ1.2~2.7:30H |
| 34 | 70.25 | 6.73 | 2.31 | 15.63 | 5.27 | | 70.22 | 6.71 | 2.27 | 15.59 | 5.21 | | δ7.0~8.0:6H, δ3.0~5.0:7H, δ1.2~2.7:28H |
| 35 | 58.17 | 5.11 | 2.73 | 12.36 | 6.25 Br | 15.42 | 58.14 | 5.07 | 2.71 | 12.39 | 6.21 Br | 1.547 | δ7.2:1H, δ3.0~5.0:3H, δ1.2~2.7:22H |
| 36 | 50.39 | 4.21 | 3.99 | 17.85 | 4.53 F Br | 8.02 11.21 | 50.36 | 4.23 | 3.92 | 17.89 | 4.48 f Br | 7.97 11.17 | δ7.2:1H, δ3.0~5.0:7H, δ1.2~2.7:22H |
| 37 | 66.57 | 5.82 | 6.91 | 20.82 | | | 66.55 | 5.75 | 6.85 | 20.86 | | | δ7.0~8.0:5H, δ3.0~5.0:9H, δ1.2~2.7:21H |
| 38 | 67.82 | 6.57 | 5.13 | 20.45 | | | 67.87 | 6.61 | 5.11 | 20.41 | | | δ7.0~8.0:2H, δ3.0~5.0:8H, δ1.2~2.7:26H |
| 39 | 66.73 | 6.55 | 5.17 | 8.91 | 5.92 Cl | 6.81 | 66.71 | 6.53 | 5.19 | 8.89 | 5.94 Cl | 6.75 | δ3.0~5.0:4H, δ1.2~2.7:31H |
| 40 | 71.52 | 6.37 | 6.71 | 10.33 | 5.12 | | 71.47 | 6.32 | 6.76 | 10.29 | 5.16 | | δ7.0~8.0:7H, δ3.0~5.0:3H, δ1.2~2.7:29H |
| 41 | 80.11 | 7.75 | 2.27 | 5.12 | 5.15 | | 80.09 | 7.52 | 2.22 | 5.08 | 5.09 | | δ7.0~8.0:7H, δ3.0~5.0:3H, δ1.2~2.7:37H |
| 42 | 73.41 | 5.37 | | 12.82 | 8.55 | | 73.38 | 5.35 | | 12.75 | 8.52 | | δ7.0~8.0:4H, δ3.7:1H, δ1.2~2.7:15H |
| 43 | 50.82 | 3.43 | | 10.17 | 6.79 F Br | 12.07 16.92 | 50.75 | 3.41 | | 10.14 | 6.77 F Br | 12.04 16.88 | δ7.2:1H, δ3.7:1H, δ1.2~2.7:14H |
| 44 | 70.25 | 6.42 | | 23.41 | | | 70.23 | 6.38 | | 23.39 | | | δ7.0:1H, δ3.0~5.0:10H, δ1.2~2.7:15H |
| 45 | 76.71 | 5.62 | | 17.83 | | | 76.65 | 5.59 | | 17.76 | | | δ7.0~8.0:4H, δ3.7:1H, δ1.2~2.7:15H |
| 46 | 75.63 | 7.47 | 3.85 | 13.15 | | | 75.59 | 7.45 | 3.83 | 13.13 | | | δ7.2:1H, δ3.0~5.0:4H, δ1.2~2.7:22H |
| 47 | 73.45 | 6.87 | | 11.7 | 7.81 | | 73.5 | 6.91 | | 11.75 | 7.85 | | δ3.7:1H, δ1.2~2.7:27H |
| 48 | 69.35 | 6.61 | | 16.11 | 8.02 | | 69.32 | 6.58 | | 16.06 | 8.04 | | δ7.2:1H, δ3.0~5.0:3H, δ1.2~2.7:22H |

TABLE 21

| No. | \multicolumn{6}{c}{Determined value} | \multicolumn{6}{c}{Calculated value} | ¹H-NMR spectrum (ppm) |
|---|---|---|---|---|---|---|---|---|---|---|---|---|---|
| | C | H | N | O | S | Others | C | H | N | O | S | Others | |
| 49 | 59.91 | 5.51 | | 10.5 | 6.92 Br | 17.35 | 59.87 | 5.46 | | 10.4 | 6.95 Br | 17.32 | δ7.2:1H, δ3.7:1H, δ1.2~2.7:23H |
| 50 | 78.92 | 7.12 | 3.22 | 10.92 | | | 78.88 | 7.08 | 3.17 | 10.87 | | | δ7.0~8.0:4H, δ3.0~5.0:3H, δ1.2~2.7:24H |
| 51 | 61.3 | 4.93 | | 10.65 | Cl | 16.17 | 61.2 | 4.91 | | 10.63 | Cl | 16.15 | δ7.2:1H, δ3.7:1H, δ1.2~2.7:20H |
| 52 | 66.53 | 5.35 | | 20.15 | 8.02 | | 66.48 | 5.33 | | 20.13 | 8.07 | | δ7.2:1H, δ3.7:1H, δ1.2~2.7:19H |

EXAMPLE 9

In each run, 0.3 part by weight of each the compounds represented by structural formulae (1) to (59) produced in Examples 1 to 8, 10 parts by eight of poly(methyl methacrylate) and 100 parts by weight of benzene were dispersed, and the resulting mixture was cast into a film on a slide glass (11.2×3.7 cm). The thickness of the cast film was adjusted to 0.1 mm. Xenon light was irradiated onto the resulting photochromic film by using a xenon long-life fadeometer (FAL-25AX-HC; output 2.5 KW; light source xenon long-life arc lamp) made by Suga Testing Instrument Co. Ltd. The initial coloration density (absorbance), maximum absorption wavelength ($\sigma_{max}$) and fatigue life ($T_{1/2}$) in accordance with JIS L 0843 and JIS B 7754 of the photochromic film were measured.

$T_{1/2}$ is defined as the time required for the color density to decrease to half of its initial value when the film is exposed to the fadeometer.

The results of measurements are shown in Tables 22 and 23. For comparison, the following (A) to (H) were also tested in the same way as above, and the fatigue life of the resulting photochromic films were measured.

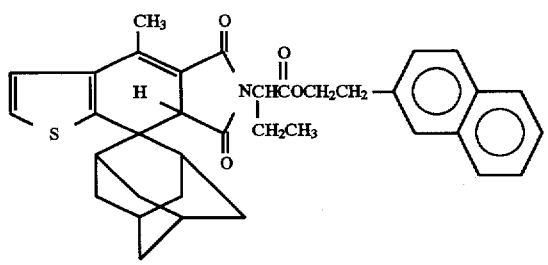

(A)

-continued
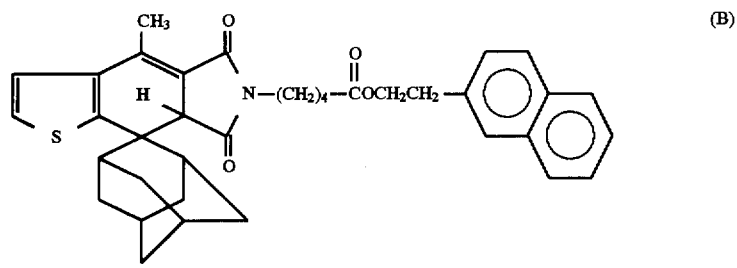
(B)
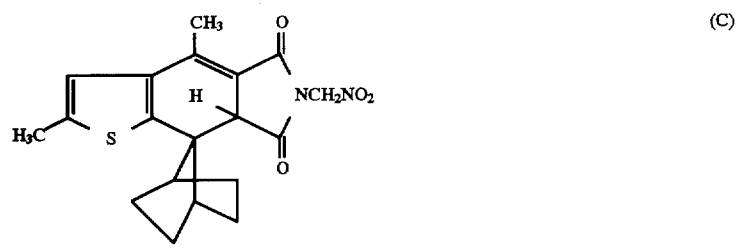
(C)
(D)
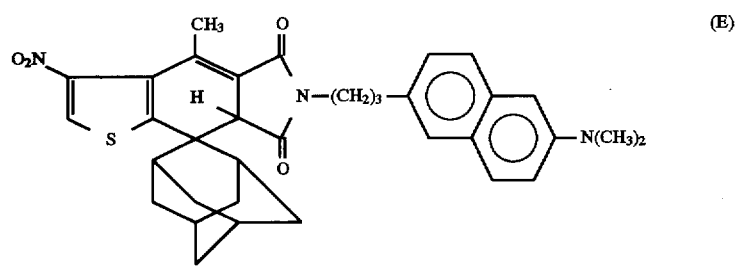
(E)
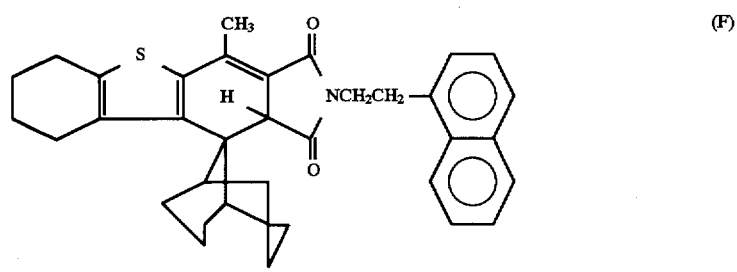
(F)
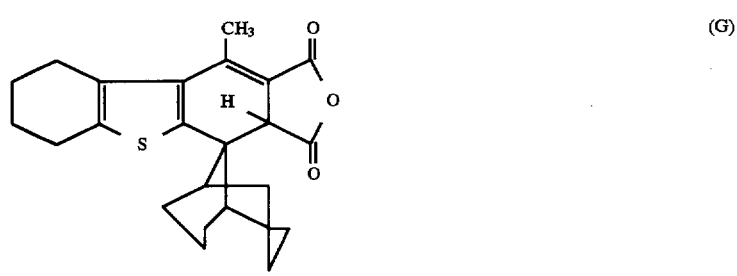
(G)

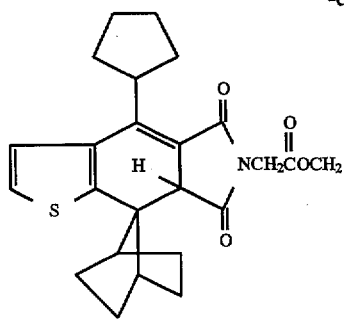

(H)

TABLE 22

| No. | Fulgimide or fulgide compound | Initial color density (%) | $T_{1/2}$ (hours) | $\lambda_{max}$ (nm) |
|---|---|---|---|---|
| 1 | (1) | 0.85 | 77 | 549 |
| 2 | (2) | 0.78 | 89 | 563 |
| 3 | (3) | 0.88 | 45 | 545 |
| 4 | (4) | 0.85 | 52 | 542 |
| 5 | (5) | 0.69 | 61 | 532 |
| 6 | (6) | 0.72 | 57 | 549 |
| 7 | (7) | 1.21 | 54 | 529 |
| 8 | (8) | 0.69 | 75 | 571 |
| 9 | (9) | 0.73 | 51 | 548 |
| 10 | (10) | 0.83 | 80 | 610 |
| 11 | (11) | 0.75 | 65 | 530 |
| 12 | (12) | 0.78 | 77 | 581 |
| 13 | (13) | 0.69 | 47 | 495 |
| 14 | (14) | 0.58 | 69 | 552 |
| 15 | (15) | 0.69 | 65 | 613 |
| 16 | (16) | 0.82 | 91 | 498 |
| 17 | (17) | 0.58 | 58 | 568 |
| 18 | (18) | 0.62 | 61 | 603 |
| 19 | (19) | 0.58 | 81 | 524 |
| 20 | (20) | 0.82 | 89 | 531 |
| 21 | (21) | 0.78 | 71 | 613 |
| 22 | (22) | 0.81 | 88 | 554 |
| 23 | (23) | 0.87 | 53 | 539 |
| 24 | (24) | 0.67 | 64 | 576 |
| 25 | (25) | 0.71 | 76 | 562 |
| 26 | (26) | 0.78 | 72 | 546 |
| 27 | (27) | 0.68 | 51 | 553 |
| 28 | (28) | 0.56 | 54 | 526 |
| 29 | (29) | 0.52 | 62 | 588 |
| 30 | (30) | 0.73 | 78 | 569 |

TABLE 23

| No. | Fulgimide or fulgide compound | Initial color density (%) | $T_{1/2}$ (hours) | $\lambda_{max}$ (nm) |
|---|---|---|---|---|
| 31 | (31) | 0.77 | 81 | 624 |
| 32 | (32) | 0.72 | 68 | 577 |
| 33 | (33) | 0.56 | 7.8 | 519 |
| 34 | (34) | 0.88 | 49 | 625 |
| 35 | (35) | 0.73 | 85 | 574 |
| 36 | (36) | 0.8 6 | 88 | 576 |
| 37 | (37) | 0.77 | 75 | 540 |
| 38 | (38) | 0.61 | 68 | 592 |
| 39 | (39) | 0.58 | 65 | 527 |
| 40 | (40) | 0.77 | 71 | 532 |
| 41 | (41) | 0.82 | 65 | 557 |
| 42 | (42) | 0.57 | 68 | 548 |
| 43 | (43) | 0.62 | 72 | 509 |
| 44 | (44) | 0.75 | 62 | 576 |
| 45 | (45) | 0.54 | 65 | 579 |
| 46 | (46) | 0.71 | 59 | 5&3 |
| 47 | (47) | 0.72 | 52 | 529 |
| 48 | (48) | 0.75 | 62 | 588 |
| 49 | (49) | 1.15 | 58 | 564 |
| 50 | (50) | 0.90 | 48 | 518 |
| 51 | (51) | 0.92 | 52 | 561 |
| 52 | (52) | 1.21 | 54 | 534 |
| 53 | (53) | 1.18 | 56 | 525 |
| 54 | (54) | 1.09 | 52 | 568 |
| 55 | (55) | 1.25 | 58 | 545 |
| 56 | (56) | 1.33 | 49 | 530 |
| 57 | (57) | 1.21 | 55 | 559 |
| 58 | (58) | 1.24 | 48 | 554 |
| 59 | (59) | 1.21 | 57 | 524 |
| Comp. 1 | (A) | 0.51 | 24 | 520 |
| Comp. 2 | (B) | 0.49 | 16 | 538 |
| Comp. 3 | (C) | 0.72 | 80 | 556 |
| Comp. 4 | (D) | 0.90 | 48 | 535 |
| Comp. 5 | (E) | 9.32 | 14 | 535 |
| Comp. 6 | (F) | 0.47 | 13 | 508 |
| Comp. 7 | (G) | 0.71 | 10 | 585 |
| Comp. 8 | (H) | 0.80 | 32 | 540 |

EXAMPLE 10

0.1 g of each of the fulgimide or fulgide compounds produced in Examples 1 to 8 was dissolved in 100 cc of silicone oil. The solution was impregnated in the surface of a lens composed of poly(allyl diglycol carbonate) at 200° C. for 1 hour. The concentration of the solution was adjusted to $1.0\times10^{-4}$ mole/g. The durability of the film was measured as in Example 9. The results are shown in Table 24.

TABLE 24

| No. | Fulgimide or fulgide compound | Initial color density (%) | $T_{1/2}$ (hours) | $\lambda_{max}$ (nm) |
|---|---|---|---|---|
| 1 | (1) | 0.78 | 82 | 554 |
| 2 | (2) | 0.71 | 91 | 568 |
| 3 | (3) | 0.81 | 49 | 550 |
| 4 | (8) | 0.63 | 80 | 578 |
| 5 | (10) | 0.82 | 85 | 615 |
| 6 | (20) | 0.73 | 95 | 535 |
| 7 | (22) | 0.70 | 93 | 559 |
| 8 | (25) | 0.65 | 79 | 565 |
| 9 | (30) | 0.68 | 85 | 571 |
| 10 | (31) | 0.69 | 86 | 616 |
| 11 | (33) | 0.49 | 80 | 525 |
| 12 | (35) | 0.67 | 90 | 580 |
| 13 | (36) | 0.77 | 95 | 582 |
| 14 | (40) | 0.70 | 74 | 535 |
| 15 | (42) | 0.51 | 71 | 553 |

TABLE 24-continued

| No. | Fulgimide or fulgide compound | Initial color density (%) | $T_{1/2}$ (hours) | $\lambda_{max}$ (nm) |
|---|---|---|---|---|
| 16 | (48) | 0.67 | 65 | 590 |
| 17 | (51) | 0.82 | 55 | 562 |
| 18 | (53) | 1.08 | 60 | 530 |
| 19 | (54) | 0.99 | 54 | 573 |
| 20 | (55) | 1.13 | 61 | 550 |

EXAMPLE 11

One hundred parts by weight of benzene, 10 parts by weight of poly(methyl methacrylate), 0.2 part by weight of the fulgimide compound obtained in Example 1 and 0.2 part by weight of each of the compounds shown in Table 25 as an ultraviolet stabilizer were mixed to form a solution. The solution was cast on a slide glass (11.2×3.7 cm) to form a cast film having a thickness of 0.1 mm.

The fatigue life of photochromic film was measured as in Example 9 by a xenon long-life fadeometer (FAL-25AX-HC made by Suga Testing Instrument Co., Ltd.). The results are shown In Table 25.

TABLE 25

| No. | Ultraviolet stabilizer | $T_{1/2}$ (hours) |
|---|---|---|
| 1 | Cyasorb UV1084 | 310 |
| 2 | Irgastab 2002 | 299 |
| 3 | Rylex NBC | 323 |
| 4 | UV Chek AM101 | 295 |
| 5 | UV Chek AM105 | 272 |
| 6 | Tinuvin 765 | 325 |
| 7 | Chimassorb 944 | 283 |
| 8 | Cyasorb 3346 | 336 |
| 9 | Tinuvin 622 | 327 |
| 10 | Spinuvex A-36 | 302 |
| 11 | Tinuvin 144 | 310 |

EXAMPLE 12

Example 11 was repeated except that the fulgimide compound obtained in Example 2 was used instead of fulgimide compound used in Example 11. The results are shown in Table 26.

TABLE 26

| No. | Ultraviolet stabilizer | $T_{1/2}$ (hours) |
|---|---|---|
| 1 | Cyasorb UV1084 | 355 |
| 2 | Irgastab 2002 | 340 |
| 3 | Rylex NBC | 369 |
| 4 | UV Chek AM101 | 336 |
| 5 | UV Chek AM105 | 308 |
| 6 | Tinuvin 765 | 373 |
| 7 | Chimassorb 944 | 325 |
| 8 | Cyasorb 3346 | 385 |
| 9 | Tinuvin 622 | 375 |
| 10 | Spinuvex A-36 | 346 |
| 11 | Tinuvin 144 | 355 |

EXAMPLE 13

Example 11 was repeated except that each of the ultraviolet stabilizers shown in Table 27 was used. The results are summarized in Table 27.

TABLE 27

| | Ultraviolet stabilizer | | | |
|---|---|---|---|---|
| Run | Type | Amount added | Proportion per 100 parts by weight of the fulgimide compound (parts by weight) | $T_{1/2}$ (hours) |
| 1 | Cyasorb UV1084 | 0.002 | 1 | 220 |
| 2 | " | 0.1 | 50 | 293 |
| 3 | " | 20 | 10000 | 367 |
| 4 | " | 0.8 | 400 | 330 |
| 5 | Tinuvin 765 | 0.002 | 1 | 213 |
| 6 | " | 0.1 | 50 | 307 |
| 7 | " | 20 | 10000 | 375 |
| 8 | " | 0.8 | 400 | 340 |

EXAMPLE 14

Example 11 was repeated except that the fulgimide or fulgide compounds shown in Table 28 were used instead of the fulgimide compounds in Example 11, and Cyasorb UV1084 was used as the ultraviolet stabilizer. The results are shown in Table 28.

TABLE 28

| No. | Fulgimide or fulgide compound | $T_{1/2}$ (hours) |
|---|---|---|
| 1 | (2) | 350 |
| 2 | (4) | 210 |
| 3 | (5) | 244 |
| 4 | (6) | 210 |
| 5 | (7) | 220 |
| 6 | (12) | 320 |
| 7 | (17) | 230 |
| 8 | (40) | 280 |
| 9 | (41) | 263 |
| 10 | (45) | 265 |
| 11 | (49) | 235 |
| 12 | (50) | 200 |
| 13 | (56) | 190 |
| 14 | (57) | 220 |
| 15 | (59) | 228 |

EXAMPLE 15

A fulgide or fulgimide compound (0.04 part) shown in Tables 29 and 30, 0.04 part of a chromene compound shown in Tables 29 and 30, 70 parts of tetraethylene glycol dimethacrylate, 15 parts of triethylene glycol dimethacrylate, 10 parts of glycidyl methacrylate, 5 parts of 2-hydroxyethyl methacrylate and 1 part of p-butyl ND as a polymerization catalyst were well mixed until they were completely dissolved. The mixed solution was injected into a mold which was made of a glass plate and a gasket formed of an ethylene-vinyl acetate copolymer, and was heated to a temperature of 35° to 90° C. in an air oven over a period of 20 hours for polymerization. After the polymerization was over, the polymer was withdrawn from the glass plate of the mold.

The resulting polymerized plate was irradiated with sunlight for 10 minutes. On this occasion, a color tone of said plate was visually observed. In this polymerized plate, the fulgide or fulgimide compound and the chromene compound were measured for fatigue life in the same manner as in Example 9. Further, a color tone of the polymerized plate was visually observed in T½ (hrs.) of the fulgide or fulgimide compound. The results are shown in Tables 29 and 30.

TABLE 29

| No. | Fulgide or fulgimide No. | Chromene compound No. | $T_{1/2}$ of fulgide or fulgimide compound (hrs.) | $T_{1/2}$ of chromene compound (hrs.) | Color tone in $T_0$ | Color tone in $T_{1/2}$ No. |
|---|---|---|---|---|---|---|
| 1 | 2 (0.05) | 2 (0.03) | 210 | 210 | brown | brown |
| 2 | 8 (0.05) | 1 (0.03) | 180 | 170 | gray | gray |
| 3 | 10 (0.05) | 3 (0.08) | 190 | 150 | green | bluish gray |
| 4 | 12 (0.05) | 4 (0.08) | 184 | 180 | gray | gray |
| 5 | 15 (0.05) | 5 (0.04) | 160 | 192 | green | light gray |
| 6 | 17 (0.05) | 5 (0.03) | 146 | 120 | gray | gray |
| 7 | 21 (0.05) | 2 (0.03) | 172 | 170 | green | green |
| 8 | 24 (0.05) | 4 (0.04) | 158 | 152 | gray | gray |
| 9 | 30 (0.05) | 1 (0.03) | 186 | 170 | gray | gray |
| 10 | 36 (0.05) | 2 (0.03) | 206 | 190 | gray | gray |
| 11 | 44 (0.05) | 3 (0.08) | 154 | 160 | gray | gray |
| 12 | 45 (0.05) | 2 (0.03) | 160 | 175 | gray | light gray |
| 13 | 46 (0.05) | 5 (0.07) | 148 | 155 | amber | amber |
| 14 | 48 (0.05) | 1 (0.04) | 154 | 148 | gray | gray |
| 15 | 54 (0.05) | 2 (0.03) | 134 | 165 | gray | brown |

Note:
Unit of parenthesized figures: parts by weight

TABLE 30

| No. | Fulgide or fulgimide No. | Chromene compound No. | $T_{1/2}$ of fulgide or fulgimide compound (hrs.) | $T_{1/2}$ of chromene compound (hrs.) | Color tone in $T_0$ | Color tone in $T_{1/2}$ No. |
|---|---|---|---|---|---|---|
| 16 | 2 (0.05) | 1/2 (0.02/0.02) | 210 | 225 | brown | brown |
| 17 | 48 (0.05) | 1/2 (0.015/0.015) | 154 | 160 | gray | gray |
| 18 | 2/48 (0.025/0.025) | 2 (0.04) | 180 | 190 | gray | gray |
| 19 | 2/48 (0.025/0.025) | 1 (0.04) | 180 | 190 | light gray | gray |
| 20 | 2/48 (0.025/0.025) | 1/2 (0.015/0.015) | 180 | 165 | gray | gray |

EXAMPLE 16

A fulgide or fulgimide compound (0.2 part) shown in Table 31, 0.2 part of a chromene compound shown in Table 31, 0.7 part of an ultraviolet light stabilizer, 70 parts of tetraethylene glycol dimethacrylate, 15 parts of triethylene glycol dimethacrylate, 10 parts of glycidyl methacrylate, 5 parts of 2-hydroxyethyl methacrylate and 1 part of p-butyl ND as a polymerization catalyst were well mixed until they were completely dissolved. A polymerized plate was obtained from the resulting mixed solution in the same manner as in Example 15, and the fulgide or fulgimide compound and the chromene compound were measured for fatigue life. The results are shown in Table 31.

TABLE 31

| Fulgide or fulgimide No. | Chromene compound No. | UV stabilizer | T₁/₂ of fulgide or fulgimide compound (hrs.) | T₁/₂ of chromene compound (hrs.) |
|---|---|---|---|---|
| 1 | 2 | 1 | Irgastab 2002 | 450 | 480 |
|   | (0.05) | (0.03) | (0.5) |   |   |
| 2 | 2 | 2 | LA-63 | 480 | 480 |
|   | (0.05) | (0.05) | (0.5) |   |   |
| 3 | 2 | 3 | Cyasorb 944 | 400 | 400 |
|   | (0.05) | (0.01) | (0.5) |   |   |
| 4 | 2 | 4 | LS-2626 | 490 | 480 |
|   | (0.05) | (0.01) | (0.4) |   |   |
| 5 | 2 | 5 | Mark LA-87 | 440 | 450 |
|   | (0.05) | (0.05) | (0.5) |   |   |
| 6 | 48 | 1 | Spinuvex A-36 | 430 | 430 |
|   | (0.05) | (0.04) | (0.6) |   |   |
| 7 | 48 | 2 | Cyasorb UV 1084 | 420 | 430 |
|   | (0.05) | (0.05) | (0.6) |   |   |
| 8 | 48 | 3 | Tinuvin 765 | 450 | 420 |
|   | (0.05) | (0.1) | (0.7) |   |   |
| 9 | 48 | 4 | UV Check AM101 | 440 | 430 |
|   | (0.05) | (0.1) | (0.4) |   |   |
| 10 | 48 | 5 | Tinuvin 622 | 450 | 430 |
|   | (0.05) | (0.05) | (0.7) |   |   |
| 11 | 2 | 2 | UV Chek AM105 | 430 | 440 |
|   | (0.05) | (0.04) | (0.7) |   |   |
| 12 | 2 | 2 | Tiniuvin 765 | 350 | 340 |
|   | (0.05) | (0.04) | (0.1) |   |   |
| 13 | 2 | 2 | Tinuvin 765 | 360 | 350 |
|   | (0.05) | (0.04) | (0.2) |   |   |
| 14 | 2 | 2 | Tinuvin 765 | 390 | 400 |
|   | (0.05) | (0.04) | (0.5) |   |   |
| 15 | 2 | 2 | Tinuvin 765 | 470 | 480 |
|   | (0.05) | (0.04) | (1.0) |   |   |
| 16 | 2 | 2 | Tinuvin 765 | 490 | 500 |
|   | (0.05) | (0.04) | (2.0) |   |   |
| 17 | 2 | 2 | Tinuvin 765 | 510 | 520 |
|   | (0.05) | (0.04) | (10.0) |   |   |

We claim:

1. A compound represented by the following general formula (I)

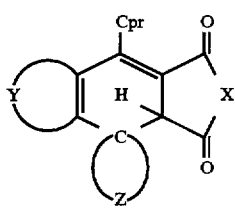

wherein

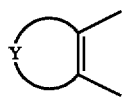

represents a 5-membered hetero-monocyclic group containing one oxygen or sulfur atom, or a condensed heterocyclic group resulting from fusion of a benzene or cyclohexene ring to the heterocyclic group, each of which is unsubstituted or is substituted by 1 to 3 atoms or groups selected from the class consisting of halogen atoms, nitro groups, cyano groups, amino groups, alkylthio groups having 1 to 4 carbon atoms, aryl groups having 6 to 10 carbon atoms, alkyl groups having 1 to 4 carbon atoms and alkoxy groups having 1 to 4 carbon atoms, Cpr represents a cyclopropyl group which is unsubstituted or is substituted with at least a substituent selected from the class consisting of halogen atoms, a nitro group, a cyano group, an amino group, alkylthio groups having 1 to 4 carbon atoms, aryl groups having 6 to 10 carbon atoms, alkyl groups having 1 to 4 carbon atoms and alkoxy groups having 1 to 4 carbon atoms,

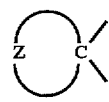

represents a norbornylidene group, a bicyclo(3.3.1) nonylidene group, or an adamantylidene group each of which is unsubstituted or is substituted with at least a substituent selected from the class consisting of halogen atoms, a hydroxyl group, alkyl groups having 1 to 4 carbon atoms, alkoxy groups having 1 to 4 carbon atoms, alkoxycarbonyl groups having 2 to 10 carbon atoms, aralkyl groups having 7 to 9 carbon atoms and aryl groups having 6 to 10 carbon atoms, and X represents an oxygen atom, the group >N—A₁—B₁—(A₂)ₘ—(B₂)ₙ—R₁₂, the group >N—A₃—A₄, or the group >N—A₃—R₁₃, in which R₁₁ represents a hydrogen atom, an alkyl group having 1 to 20 carbon atoms, or an aryl group having 6 to 10 carbon atoms, A₁ and A₂ are identical or different and each represents an alkylene group having 1 to 10 carbon atoms, an alkylidene group having 2 to 10 carbon atoms, a cycloalkylene group having 3 to 10 carbon atoms or an alkylcycloalkanediyl group having 6 to 10 carbon atoms, $B_1$ and $B_2$ are identical or different, and each represents

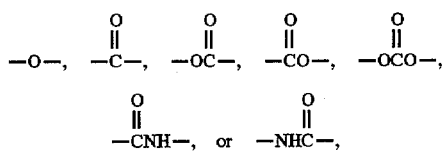

m and n, independently from each other, represent 0 or 1, provided that when m is 0, n is also 0, $R_{12}$ represents an alkyl group having 1 to 10 carbon atoms, a naphthyl group or a naphthylalkyl group having 1 to 4 carbon atoms in the alkyl moiety, the alkyl group having 1 to 10 carbon atoms being unsubstituted or substituted by 1 to 3 atoms or groups selected from the class consisting of halogen atoms, cyano groups and nitro groups, and the naphthyl or naphthylalkyl group being unsubstituted or substituted by 1 to 3 atoms or groups selected from the class consisting of halogen atoms, cyano groups, nitro groups, alkylamino groups having 1 to 3 carbon atoms and alkoxy groups having 1 to 3 carbon atoms, $A_3$ represents and alkylene group having 1 to 10 carbon atoms, an alkylidene group having 2 to 10 carbon atoms, a cycloalkylene group having 3 to 10 carbon atoms, or an alkylcycloalkanediyl group having 6 to 10 carbon atoms, $A_4$ represents a naphthyl group which is unsubstituted or is substituted by 1 to 3 atoms or groups selected from the class consisting of halogen atoms, cyano groups, nitro groups, alkylamino groups having 1 to 3 carbon atoms and alkoxy groups having 1 to 3 carbon atoms, and $R_{13}$ represents a halogen atom, a cyano group or a nitro group.

2. The compound of claim 1 in which X is the group $>N-A_3-R_{13}$.

3. The compound of claim 1 in which X is the group $>N-A_1-B_1-(A_2)_m-(B_2)_n-R_{12}$.

4. The compound of claim 1 in which X is the group $>N-A_3-A_4$.

5. A process for producing a compound represented by the following general formula (I)

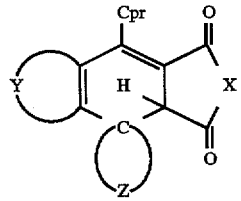

(I)

wherein

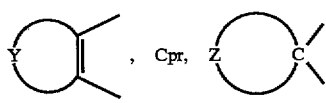

and X are as defined below with regard to general formula (I), which comprises cyclizing a compound represented by the following general formula (II)

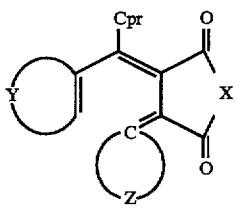

(II)

wherein

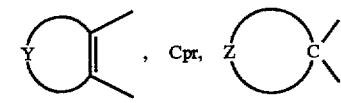

and X are as defined below with regard to general formula (I), or reacting the compound of general formula (II) with an amine compound represented by the following general formula (III-a), (III-b), (III-c) or (III-d)

$H_2N-R_{11}$ (III-a)

$H_2N-A_1-B_1-(A_2)_m-(B_2)_n-R_{12}$ (III-b)

$H_N-A_3-R_4$ (III-c)

$H_2N-A_3-R_{13}$ (III-d)

wherein $R_{11}$, $R_{12}$, $R_{13}$, $A_1$, $A_2$, $A_3$, $A_4$, $B_1$, $B_2$, m and n are as defined below, and then cyclizing the reaction product, wherein

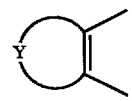

represents a 5-membered hetero-monocyclic group containing one oxygen or sulfur atom, or a condensed heterocyclic group resulting from fusion of a benzene or unsubstituted or is substituted by 1 to 3 atoms or groups selected from the class consisting of halogen atoms, nitro groups, cyano groups amino groups, alkylthio groups having 1 to 4 carbon atoms, aryl groups having 6 to 10 carbon atoms, alkyl groups having 1 to 4 carbon atoms and alkoxy groups having 1 to 4 carbon atoms, Cpr represents a cyclopropyl group which is unsubstituted or is substituted with at least a substituent selected from the class consisting of halogen atoms, a nitro group a cyano group, an amino group, alkylthio groups having 1 to 4 carbon atoms, aryl groups having 6 to 10 carbon atoms, alkyl groups having 1 to 4 carbon atoms and alkoxy groups having 1 to 4 carbon atoms,

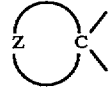

represents a norbornylidene group, a bicyclo(3.3.1) nonylidene group, or an adamantylidene group each of which is unsubstituted or is substituted with at least a substituent selected from the class consisting of halogen atoms, a hydroxyl group, alkyl group having 1 to 4 carbon atoms, alkoxy groups having 1 to 4 carbon atoms, alkoxycarbonyl groups having 2 to 10 carbon atoms, aralkyl groups having 7 to 9 carbon atoms and aryl groups having 6 to 10 carbon atoms, and X represents an oxygen atom, the group >N—$A_1$—$B_1$—$(A_2)_m$—$(B_2)_n$—$R_{12}$, the group >N—$A_3$—$A_4$, or the group >N—$A_3$—$R_{13}$, in which $R_{11}$ represents a hydrogen atom, an alkyl group having 1 to 20 carbon atoms, or an aryl group having 6 to 10 carbon atoms, $A_1$ and $A_2$ are identical or different and each represents an alkylene group having 1 to 10 carbon atoms, an alkylidene group having 2 to 10 carbon atoms, a cycloalkylene group having 3 to 10 carbon atoms or an alkylcycloalkanediyl group having 6 to 10 carbon atoms, $B_1$ and $B_2$ are identical or different, and each represents $$-O-, \quad -\overset{O}{\underset{\|}{C}}-, \quad -O\overset{O}{\underset{\|}{C}}-, \quad -\overset{O}{\underset{\|}{C}}O-, \quad -O\overset{O}{\underset{\|}{C}}O-,$$

$$-\overset{O}{\underset{\|}{C}}NH-, \quad \text{or} \quad -NH\overset{O}{\underset{\|}{C}}-,$$

m and n, independently from each other, represent 0 or 1, provided that when m is 0, n is also 0, $R_{12}$ represents an alkyl group having 1 to 10 carbon atoms, a naphthyl group or a naphthylalkyl group having 1 to 4 carbon atoms in the alkyl moiety, the alkyl group having 1 to 10 carbon atoms being unsubstituted or substituted by 1 to 3 atoms or groups selected from the glass consisting of halogen atoms, cyano group and nitro groups, and the naphthyl or naphthylalkyl group being unsubstituted or substituted by 1 to 3 atoms or groups selected from the class consisting of halogen atoms, cyano groups, nitro groups, alkylamino groups having 1 to 3 carbon atoms and alkoxy groups having 1 to 3 carbon atoms, $A_3$ represents an alkylene group having 1 to 10 carbon atoms, an alkylidene group having 2 to 10 carbon atoms, a cycloalkylene group having 3 to 10 carbon atoms, or an alkylcycloalkanediyl group having 6 to 10 carbon atoms, $A_4$ represents a naphthyl group which is unsubstituted or is substituted by 1 to 3 atoms or groups selected from the class consisting of halogen atoms, cyano groups, nitro groups alkylamino groups having 1 to 3 carbon atoms and alkoxy groups having 1 to 3 carbon atoms, and $R_{13}$ represents a halogen atom, a cyano group or a nitro group.

6. A process for producing a compound represented by the following general formula (I)

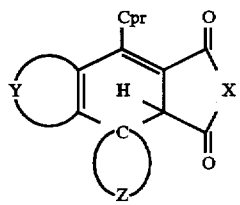
(I)

wherein

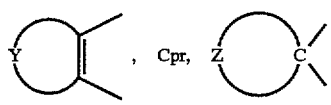

and X are as defined below with regard to general formula (I), provided that an oxygen atom is excluded from the definition of X, which comprises reacting an imide compound represented by the following general formula (IV)

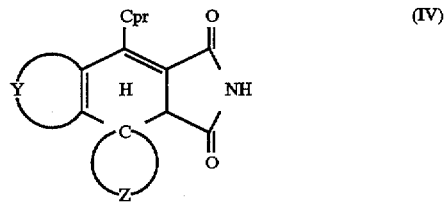
(IV)

wherein

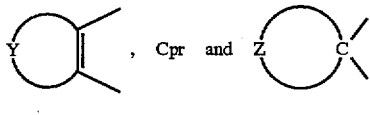

are as defined with regard to general formula (I), with an alkali metal, and then reacting the product with a bromine compound represented by the following general formula (V-a), (V-b), (V-c) or (V-d)

| | |
|---|---|
| Br—$R_{11}$ | (V-a) |
| Br—$A_1$—$B_1$—$(A_2)_m$—$(B_2)_n$—$R_{12}$ | (V-b) |
| Br—$A_3$—$A_4$ | (V-c) |
| Br—$A_3$—$R_{13}$ | (V-d) | wherein $R_{11}$, $R_{12}$, $R_{13}$, $A_1$, $A_2$, $A_3$, $A_4$, $B_1$, $B_2$, m and n are as defined with regard to the formula (I), wherein

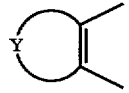

represents a 5-membered hetero-monocyclic group containing one oxygen or sulfur atom, or a condensed heterocyclic group resulting from fusion of a benzene or cyclohexene ring to the heterocyclic group, each of which is unsubstituted or is substituted by 1 to 3 atoms or groups selected from the class consisting of halogen atoms, nitro groups, cyano groups, amino groups, alkylthio groups having 1 to 4 carbon atoms, aryl groups having 6 to 10 carbon atoms, alkyl groups having 1 to 4 carbon atoms and alkoxy groups having 1 to 4 carbon atoms, Cpr represents a cyclopropyl group which is unsubstituted or is substituted with at least a substituent selected from the class consisting of halogen atoms, a nitro group, a cyano group, an amino group, alkylthio groups having 1 to 4 carbon atoms, aryl groups having 6 to 10 carbon atoms, alkyl groups having 1 to 4 carbon atoms and alkoxy groups having 1 to 4 carbon atoms, represents a norbornylidene group, a bicyclo(3.3.1) nonylidene group, or an adamantylidene group each of which is unsubstituted or is substituted with at least a substituent selected from the class consisting of halogen atoms, hydroxyl group, alkyl groups having 1 to 4 carbon atoms, alkoxy groups having 1 to 4 carbon atoms, alkoxycarbonyl groups having 2 to 10 carbon atoms, aralkyl groups having 7 to 9 carbon atoms and aryl groups having 6 to 10 carbon atoms, and X represents an oxygen atom, the group >N—$A_1$—$B_1$—$(A_2)_m$—$(B_2)_n$—$R_{12}$, the group >N—$A_3$—$A_4$, or the group >N—$A_3$—$R_{13}$, in which $R_{11}$ represents a hydrogen atom, an alkyl group having 1 to 20 carbon atoms, or an aryl group having 6 to 10 carbon atoms, $A_1$ and $A_2$ are identical or different and each represents an alkylene group having 1 to 10 carbon atoms, an alkylidene group having 2 to 10 carbon atoms, a cycloalkylene group having 3 to 10 carbon atoms or an alkylcycloalkanediyl group having 6 to 10 carbon atoms, $B_1$ and $B_2$ are identical or different, and each represents $$-O-, \quad -\overset{O}{\underset{\|}{C}}-, \quad -O\overset{O}{\underset{\|}{C}}-, \quad -\overset{O}{\underset{\|}{C}}O-, \quad -O\overset{O}{\underset{\|}{C}}O-,$$

$$-\overset{O}{\underset{\|}{C}}NH-, \quad \text{or} \quad -NH\overset{O}{\underset{\|}{C}}-,$$

m and n, independently from each other, represent 0 or 1, provided that when m is 0, n is also 0, $R_{12}$ represents an alkyl group having 1 to 10 carbon atoms, a naphthyl group or a naphthylalkyl group having 1 to 4 carbon atoms in the alkyl moiety, the alkyl group having 1 to 10 carbon atoms being unsubstituted or substituted by 1 to 3 atoms or groups selected from the class consisting of halogen atoms, cyano groups and nitro groups, and the naphthyl or naphthylalkyl group being unsubstituted or substituted by 1 to 3 atoms or groups selected from the class consisting of halogen atoms, cyano groups, nitro groups, alkylamino groups having 1 to 3 carbon atoms and alkoxy groups having 1 to 3 carbon atoms, $A_3$ represents and alkylene group having 1 to 10 carbon atoms, an alkylidene group having 2 to 10 carbon atoms, a cycloalkylene group having 3 to 10 carbon atoms, or an alkylcycloalkanediyl group having 6 to 10 carbon atoms, $A_4$ represents a naphthyl group which is unsubstituted or is substituted by 1 to 3 atoms or groups selected from the class consisting of halogen atoms, cyano groups, nitro groups, alkylamino groups having 1 to 3 carbon atoms and alkoxy groups having 1 to 3 carbon atoms, and $R_{13}$ represents a halogen atom, a cyano group or a nitro group.

7. A composition comprising a high-molecular weight polymer and a compound represented by the following general formula [I]

wherein and X are as defined in claim 1.

8. The composition of claim 7 which further comprises an ultraviolet stabilizer.

9. The composition of claim 8 in which the ultraviolet stabilizer is a light extinguisher for oxygen in the singlet state or a hindered amine light stabilizer.

10. The composition of claim 7 which further comprises the chromene compound.

11. The composition of claim 10 in which the chromene compound is represented by the following general formula [V]

wherein $R_1$, $R_2$, $R_3$ and $R_4$ are the same or different, and each represents a hydrogen atom, an alkyl group, an aryl group, a substituted amino group or a saturated heterocyclic group, $R_3$ and $R_4$ may together form a ring, and the group Y is a divalent aromatic hydrocarbon group or a divalent unsaturated heterocyclic group each of which may have a substituent.

12. A photochromic lens composed of the composition of claim 7.

13. A compound of claim 1 selected from the group consisting of:

(1) 4-cyclopropyl-6,7-dihydrdo-N-methoxycarbonylmethylspirobenzo[5,6-b]thiophenedicarboxyimido-7,7'-bicyclo[2.2.1]heptane;

(2) N-cyanomethyl-4-cyclopropyl-6,7-dihydridospirobenzo[5,6-b]thiophenedicarboxyimido-7.7'-bicyclo[2.2.1]heptane;

(3) 2-bromo-4-cyclopropyl-6,7-dihydrido-N-(β-naphtylethyl)spirobenzo[5,6-b]thiophenedicarboxyimido-7'9'-bicyclo[3.3.1]nonane;

(4) 2-bromo-4-cyclopropyl-6,7-dihydridospirobenzo[5,6-b]thiophenedicarboxyanhydride-7,2'-tricyclo[3.1.1$_{3,7}$]decane;

(5) 4-cyclopropyl-6,7-dihydrido-2-methyl-N-nitromethylspirobenzo[5,6-]thiophenedicarboxyimide-7,7'-bicyclo[2.2.1]heptane;

(6) 4-(2"-methylcyclopropyl)-6,7-dihydrido-N-methylcarbonylmethyl-2-phenylspirobenzo[5,6-b]thiophenedicarboxyimido-7,7'-bicyclo[2,2,1]heptane;

(7) 3,4-dihydro-5,7-dimethoxy-N-(O-naphtylmethyl)-1-(2",3"-tetramethylcyclopropyl)spirophthalenedicarboxyimido-4,7'-bicyclo[2.2.1]heptane;

(8) N-cyanomethyl-6,7-dihydro-4-(2-phenoxycyclopropyl)spirobenzo[6,5-b]furancarboxyimido-7,7'-bicyclo[2.2.1]heptane;

(9) 2-bromo-4-(2",3"-dichloromethyl)-6,7-dihydro-N-isobutoxycarbonylmethylspirobenzo[5,6-b]thiophenecarboxyimide-7,9'-bicyclo[3.3.1]nonane;

(10) 6-cyclopropyl-8,9-dihydrospirodibenzo-[5,6-b:d])thiophenecarboxyanhydride-9,7'-bicyclo[2.2.1]heptane;

(11) 4-cyclopropyl-6,7'-1,2-dimethylspiroindolecarboxyanhydride-7,9'-bicyclo[3.3.1]nonane;

(12) 2-bromo-4-cyclopropyl-3',3'-dimethylspirobenzo[5,6-b]thiophenecarboxyimido-7,9'-bicyclo[3.3.1]nonane;

(13) 2-bromo-7-cyclopropyl-4,5-dihydro-N-methylcarboxymethylspirobenzo[5,6-b]thiophenecarboxyimido-4,2-tricyclo[3.3.1.1$^{3,7}$]decane;

(14) 1,2,3,4,8,9-hexahydro-N-(α-naphtylpentyl)-6(2"-methylcyclopropyl)spirodibenzo[5,6-b:d]thiophenecarboxyimido-9,2'-tricyclo[3.3.1.1$^{3,7}$]decane; and

(15) 4-cyclopropyl-6,7-dihydrido-2-nitrospirobenzo[5.6-b]thiophenedicarboxyanhydride-7,2'-tricyclo[3.3.1.1$^{3.7}$]decane.

14. The compound of claim 1 in which

represents a 5-membered hetero-monocylic group containing a sulfur atom which is unsubstituted or is substituted by 1 to 3 atoms or groups selected from the class consisting of halogen atoms, nitro groups, cyano groups, amino groups, alkylthio groups having 1 to 4 carbon atoms, alkoxy groups having 1 to 4 carbon atoms, aryl groups having 6 to 10 carbon atoms, and alkyl groups having 1 to 4 carbon atoms.

* * * * *